(12) United States Patent
Huang

(10) Patent No.: US 9,943,383 B2
(45) Date of Patent: Apr. 17, 2018

(54) BIASED PIVOTING SLIDE ORTHODONTIC BRACKET

(71) Applicant: Ormco Corporation, Orange, CA (US)

(72) Inventor: Stanley S. Huang, Irvine, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 14/962,703

(22) Filed: Dec. 8, 2015

(65) Prior Publication Data

US 2016/0175073 A1 Jun. 23, 2016

Related U.S. Application Data

(60) Provisional application No. 62/094,451, filed on Dec. 19, 2014.

(51) Int. Cl.
| | |
|---|---|
| A61C 3/00 | (2006.01) |
| A61C 7/28 | (2006.01) |
| A61C 7/12 | (2006.01) |
| A61C 7/30 | (2006.01) |

(52) U.S. Cl.
CPC .............. *A61C 7/287* (2013.01); *A61C 7/12* (2013.01); *A61C 7/285* (2013.01); *A61C 7/30* (2013.01)

(58) Field of Classification Search
CPC .......... A61C 7/287; A61C 7/12; A61C 7/285; A61C 7/30
USPC ..................................................... 433/8–16
See application file for complete search history.

(56) References Cited

U.S. PATENT DOCUMENTS

| | | |
|---|---|---|
| 4,103,423 A | 8/1978 | Kessel |
| 4,492,573 A | 1/1985 | Hanson |
| 5,094,614 A | 3/1992 | Wildman |
| 5,275,557 A | 1/1994 | Damon |

(Continued)

FOREIGN PATENT DOCUMENTS

| | | |
|---|---|---|
| EP | 1063936 A1 | 1/2001 |
| EP | 1508310 A2 | 2/2005 |

(Continued)

OTHER PUBLICATIONS

European Patent Office, European Search Report in EP Application No. 15200217.6, dated Apr. 26, 2016.

(Continued)

*Primary Examiner* — Heidi M Eide
(74) *Attorney, Agent, or Firm* — Wood Herron & Evans LLP

(57) ABSTRACT

An orthodontic bracket includes a bracket body and a ligating slide. The bracket body includes an aperture and an archwire slot. The ligating slide is slidable relative to the archwire slot between an opened position and a first closed position and is pivotable to an angular position in a second closed position. The orthodontic bracket further includes a resilient member that is coupled to the ligating slide and is slidable in the aperture. The ligating slide defines a first height from the base surface having a first value, and in the second closed position, the ligating slide defines a second height from the base surface that is greater than the first value. The bracket body includes a slide support portion having at least one wing extending laterally therefrom. The wing is tapered in thickness. The slide support portion defines a pivot point about which the ligating slide is pivotable.

23 Claims, 17 Drawing Sheets

(56) References Cited

U.S. PATENT DOCUMENTS

| | | | |
|---|---|---|---|
| 5,322,435 A | 6/1994 | Pletcher | |
| 5,356,288 A | 10/1994 | Cohen | |
| 5,466,151 A | 11/1995 | Damon | |
| 5,474,445 A | 12/1995 | Voudouris | |
| 5,857,849 A | 1/1999 | Kurz | |
| 5,857,850 A | 1/1999 | Voudouris | |
| 5,971,753 A | 10/1999 | Heiser | |
| 6,071,118 A | 6/2000 | Damon | |
| 6,071,119 A | 6/2000 | Christoff et al. | |
| 7,416,408 B2 | 8/2008 | Farzin-Nia et al. | |
| 7,621,743 B2 | 11/2009 | Bathen et al. | |
| 7,674,110 B2 | 3/2010 | Oda | |
| 7,857,618 B2 | 12/2010 | Abels et al. | |
| 7,963,768 B2 | 6/2011 | Hilliard | |
| 8,033,824 B2 | 10/2011 | Oda et al. | |
| 8,251,696 B2 | 8/2012 | Rodriguez et al. | |
| 8,585,398 B2 | 11/2013 | Yeh et al. | |
| 8,998,607 B2 | 4/2015 | Oda | |
| 9,364,298 B2 | 6/2016 | Huang | |
| 2005/0221248 A1* | 10/2005 | Navarro | A61C 7/287 433/11 |
| 2006/0154196 A1 | 7/2006 | Oda | |
| 2007/0224569 A1 | 9/2007 | Oda | |
| 2007/0248928 A1 | 10/2007 | Damon | |
| 2007/0269763 A1 | 11/2007 | Schendell-Groling | |
| 2008/0045956 A1 | 2/2008 | Songer et al. | |
| 2010/0173256 A1 | 7/2010 | Rodriguez et al. | |
| 2010/0285420 A1 | 11/2010 | Oda | |
| 2012/0058442 A1* | 3/2012 | Oda | A61C 7/287 433/11 |
| 2012/0064476 A1 | 3/2012 | Sabilla | |
| 2012/0129119 A1 | 5/2012 | Oda | |
| 2012/0288816 A1 | 11/2012 | Dupray et al. | |
| 2014/0127638 A1 | 5/2014 | Huang | |
| 2014/0272752 A1 | 9/2014 | Huang | |

FOREIGN PATENT DOCUMENTS

| | | |
|---|---|---|
| WO | 2011062603 A1 | 5/2011 |
| WO | 2012145144 A1 | 10/2012 |

OTHER PUBLICATIONS

United States Patent and Trademark Office, Office Action issued in U.S. Appl. No. 12/752,411, dated Jul. 12, 2013.
United States Patent and Trademark Office, Office Action issued in U.S. Appl. No. 12/752,411, dated Aug. 21, 2012.
United States Patent and Trademark Office, Office Action issued in U.S. Appl. No. 12/752,411, dated Oct. 27, 2011.
European Patent and Trademark Office, European Search Report in EP Application No. 10250843, dated Mar. 7, 2011.
European Patent and Trademark Office, European Search Report in EP Application No. 13191984.7, dated Mar. 3, 2014.
European Patent and Trademark Office, European Search Report in EP Application No. 14159463, dated Jul. 1, 2014.
U.S. Patent and Trademark Office, Office Action in U.S. Appl. No. 14/205,674, dated Nov. 3, 2015.
U.S. Patent and Trademark Office, Office Action in U.S. Appl. No. 14/205,674, dated Mar. 2, 2016.
U.S. Patent and Trademark Office, Office Action in U.S. Appl. No. 14/072,310, dated Mar. 27, 2015.
U.S. Patent and Trademark Office, Office Action in U.S. Appl. No. 14/072,310, dated Oct. 27, 2015.
U.S. Patent and Trademark Office, Notice of Allowance in U.S. Appl. No. 14/072,310, dated Feb. 16, 2016.

* cited by examiner

BIASED PIVOTING SLIDE ORTHODONTIC BRACKET

CROSS REFERENCE TO RELATED CASES

This application claims priority to U.S. Provisional Patent Application Ser. No. 62/094,451 filed Dec. 19, 2014, the disclosure of which is incorporated by reference herein in its entirety.

TECHNICAL FIELD

The invention relates generally to orthodontic brackets and, more particularly, to self-ligating orthodontic brackets having movable closure members.

BACKGROUND

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

While such self-ligating brackets are generally successful in achieving their intended purpose, there remain some drawbacks. By way of example, in some instances controlling the rotation of the teeth, such as near the finishing stages of orthodontic treatment, can be problematic. While there may be several factors that cause a reduction in rotational control, it is believed that one of the major causes is the loose fit of the archwire within the archwire slot of the bracket when the movable member is closed. When the movable member is closed, the bracket body and the movable member collectively form a closed lumen for capturing the archwire. A close fit between the lumen and the archwire is believed to be important for achieving excellent rotational control during orthodontic treatment.

The close fit between the archwire and the archwire slot when the movable member is closed may be affected by several factors including, for example, the tolerances of the manufacturing process used to form the bracket body and the movable member. When the orthodontic bracket is assembled, the various tolerances may "stack up" so as to provide a relatively loose fit between the archwire and the closed lumen provided by the bracket body and movable member. As noted above, such a loose fit is believed to result in a diminished capacity to control the rotation of the teeth.

In addition, to allow the movable member to move relative to the bracket body between the opened and closed positions, there must be some clearance between the bracket body and the movable member. In other words, there are typically some tolerances in the manufacturing process that provide a clearance. Yet, these tolerances stack up to provide a lumen which may vary significantly in its labial-lingual dimension between brackets and therefore may provide a relatively loose fit with the archwire in some instances.

Thus, while self-ligating brackets have been generally successful, manufacturers of such brackets continually strive to improve their use and functionality. In this regard, there remains a need for self-ligating orthodontic brackets that provide improved rotational control during orthodontic treatment, such as during the finishing stages thereof.

SUMMARY

To address the drawbacks of existing orthodontic brackets, an orthodontic bracket for coupling an archwire with a tooth includes a bracket body and a ligating slide. The bracket body includes an aperture and an archwire slot for receiving an archwire therein. The ligating slide is slidable relative to the archwire slot between an opened position in which an archwire may be inserted in the archwire slot and a first closed position in which the ligating slide retains the archwire in the archwire slot. The ligating slide is pivotable relative to the archwire slot to a second closed position in which the ligating slide retains the archwire in the archwire slot. The second closed position is different from the first closed position.

In one embodiment, the second closed position defines a labial-lingual height between the ligating slide and a base surface of the archwire slot that is greater than a labial-lingual height between the ligating slide and the base surface of the archwire slot in the first closed position. The ligating slide is pivotable relative to the bracket body to an angular position that exceeds normal tolerance stack up of existing orthodontic brackets. The orthodontic bracket further includes a resilient member that is coupled to the ligating slide and is slidable in the aperture.

In one embodiment, the ligating slide is pivotable to an angle between the first closed position and the second closed position that is greater than about 5° to about 20°. In one embodiment, the ligating slide is pivotable to an angle between the first closed position and the second closed position that is from about 10° to about 20°.

In one embodiment, the archwire slot includes opposing slot surfaces extending from a base surface and in the first closed position, the ligating slide defines a first height from the base surface having a first value and in the second closed position, the ligating slide defines a second height from the base surface that is at least about 0.002 inch greater than the first value.

In one embodiment, the bracket body includes a slide support portion having at least one wing extending laterally therefrom. The wing is tapered in thickness along the length thereof. The slide support portion defines a pivot point about which the ligating slide is pivotable between the first closed position and the second closed position. The tapered wing determines a first gap between the slide support portion and the ligating slide in the first closed position and a second gap between the slide support portion and the ligating slide in the second closed position. In one embodiment, the ligating slide includes a uniformly dimensioned recess and the wing resides within the recess during sliding movement of the ligating slide.

In one embodiment, at the first closed position there is a gap between the recess and the wing. In one embodiment, the recess defines a shoulder and at the second closed position, the shoulder contacts the wing.

In one embodiment, the bracket body includes a support surface and the ligating slide includes a sliding surface that faces the support surface when the ligating slide is in the first closed position, and when the ligating slide is pivoted to the second closed position, the support surface and the sliding surface contact at a pivot point and an angle of greater than about 5° is formed between the support surface and the sliding surface at the pivot point.

In one embodiment, the pivot point is at a peripheral edge of the support surface from the archwire slot.

In one embodiment, the resilient member imposes a biasing force on the ligating slide in each of the first closed position and the second closed position.

In one embodiment, the ligating slide does not pivot about the resilient member.

BRIEF DESCRIPTION OF THE DRAWINGS

The accompanying drawings, which are incorporated in and constitute a part of this specification, illustrate embodiments of the invention and together with the detailed description given below, serve to explain various aspects of the invention.

DETAILED DESCRIPTION

Figure 1:
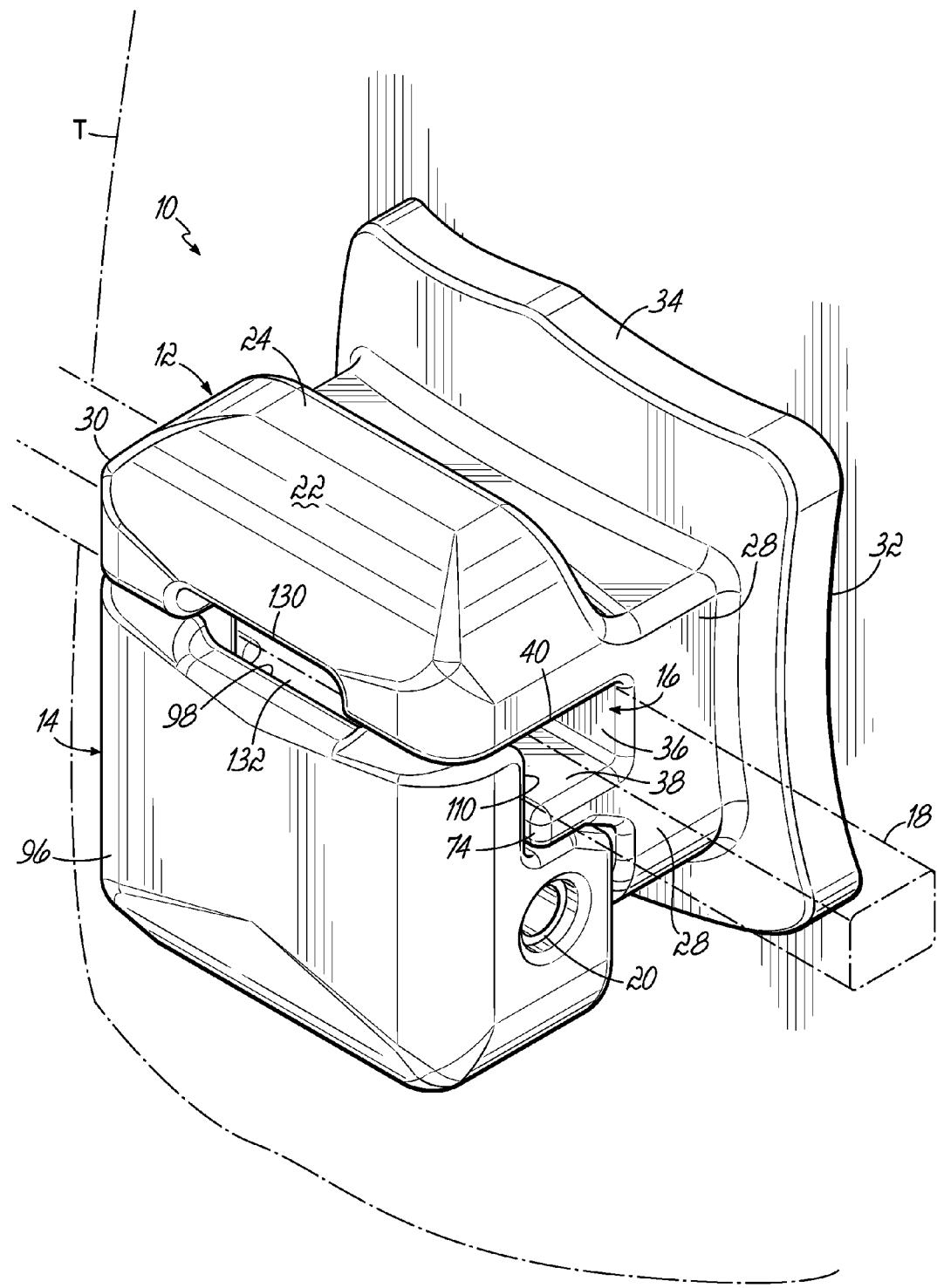
FIG. 1 is a perspective view of an orthodontic bracket according to one embodiment of the invention attached to a tooth, with a slide member shown in the closed position.
Figure 2:
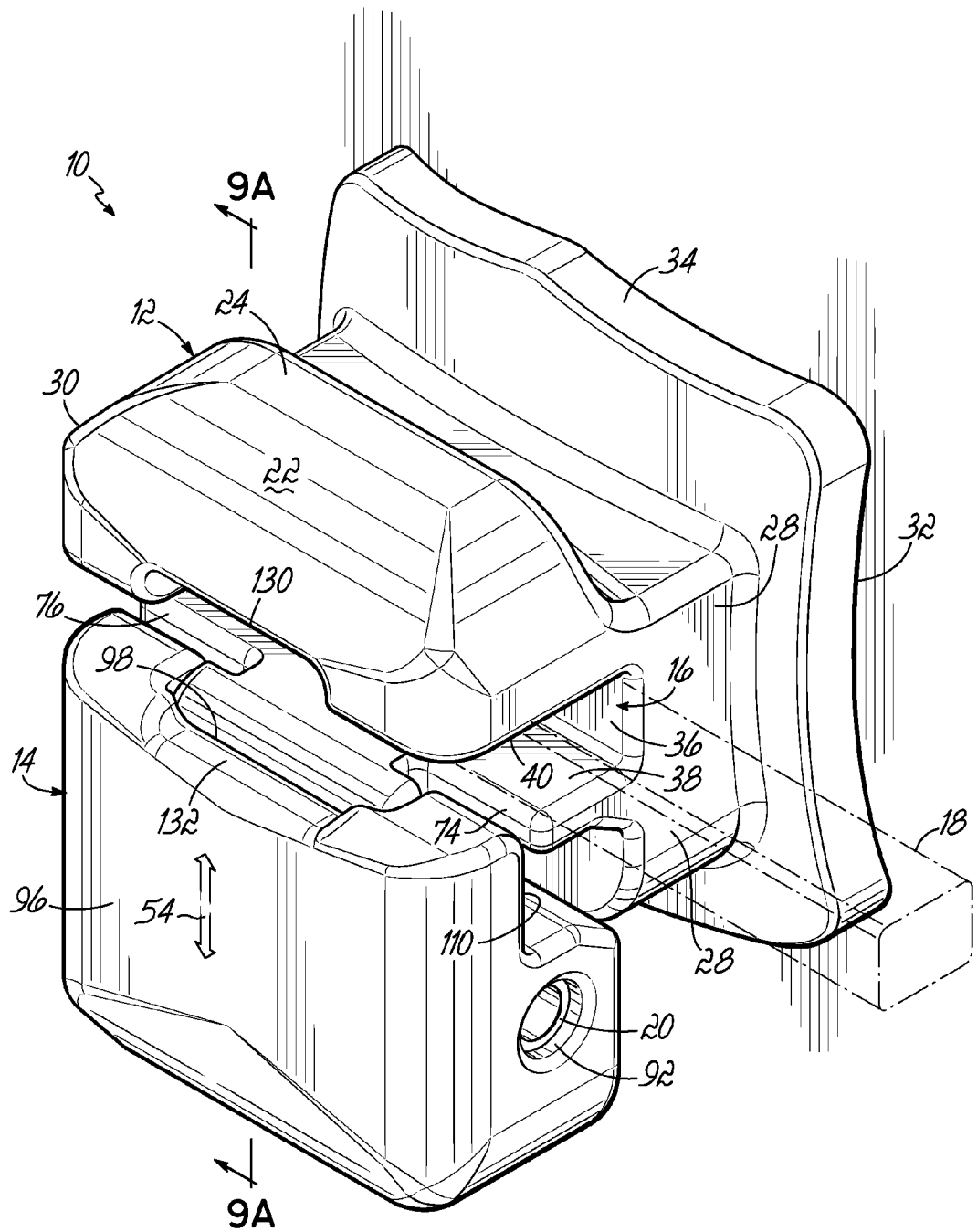
FIG. 2 is a perspective view of the orthodontic bracket shown in FIG. 1 with the slide member shown in the opened position.

Referring now to the drawings, and to FIGS. 1 and 2 in particular, an orthodontic bracket 10 includes a bracket body 12 and a movable closure member coupled to the bracket body 12. In one embodiment, the movable closure member includes a slide member, such as, a ligating slide 14, slidably coupled with the bracket body 12. The bracket body 12 includes an archwire slot 16 formed therein configured to receive an archwire 18 (shown in phantom) for applying corrective forces to the teeth. The ligating slide 14 is slidable between a closed position (FIG. 1) in which the archwire 18 is retained within a lumen defined by the archwire slot 16 and the ligating slide 14, and an opened position (FIG. 2) in which the archwire 18 is insertable into the archwire slot 16. The ligating slide 14 is also movable in an outward direction relative to the archwire slot 16, which may be generally perpendicular to the sliding motion of the ligating slide 14, to a second closed position. The second closed position may be a fixed stop predetermined by the bracket body 12 and the ligating slide 14. The second closed position may also define a lumen for retaining the archwire 18 therein. However, unlike a U-shaped clip or other flexible retaining member, the ligating slide 14 according to embodiments of the invention does not flex appreciably at loads observed during normal orthodontic treatment. The bracket body 12 and ligating slide 14 collectively form an orthodontic bracket 10 for use in corrective orthodontic treatments.

In addition to the above, the orthodontic bracket 10 further includes a resilient member coupled to the ligating slide 14 and configured to engage at least a portion of the bracket body 12. As explained in more detail below, the resilient member, which in one embodiment includes a tubular pin 20 (shown in FIGS. 1 and 2), provides a force for biasing the ligating slide 14 at least partly in the direction of the sliding or translational motion of the ligating slide 14. The tubular pin 20 may also or alternatively bias the ligating slide 14 toward the archwire slot 16. While the resilient member is shown herein as a tubular pin, the invention is not limited to this particular configuration, as other resilient members may be configured in accordance with the invention disclosed herein. It is believed that providing a biasing force in conjunction with the structural features of the orthodontic bracket 10, as described below, reduces the effects of the tolerance in the archwire slot 16 in combination with other tolerances. By limiting the overall effect of the tolerances, the working dimensions of the archwire slot 16 may be more precisely known. This ultimately allows the clinician to more precisely predict and control tooth movement with the orthodontic bracket 10. It will be appreciated that improving the clinician's control of tooth movement may comparatively reduce treatment time for a particular patient.

In conjunction with other structural features of the bracket body 12, described in detail below, the resilient member 20 enables the bracket 10 to actively ligate an archwire that is larger in height dimension than the height (e.g., labial-lingual dimension) of the archwire slot 16. Thus, a clinician may select an oversized archwire and actively ligate that archwire with the slide 14 during treatment. This may improve the rotational control requirements typically desired during the final stages of orthodontic treatment and may bring about completion of orthodontic treatment more quickly than self-ligating orthodontic brackets that are only capable of passive ligation.

The orthodontic bracket 10, unless otherwise indicated, is described herein using a reference frame attached to a labial surface of an anterior tooth on the lower jaw. Consequently, as used herein, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the invention to a particular location or orientation.

Figure 3:
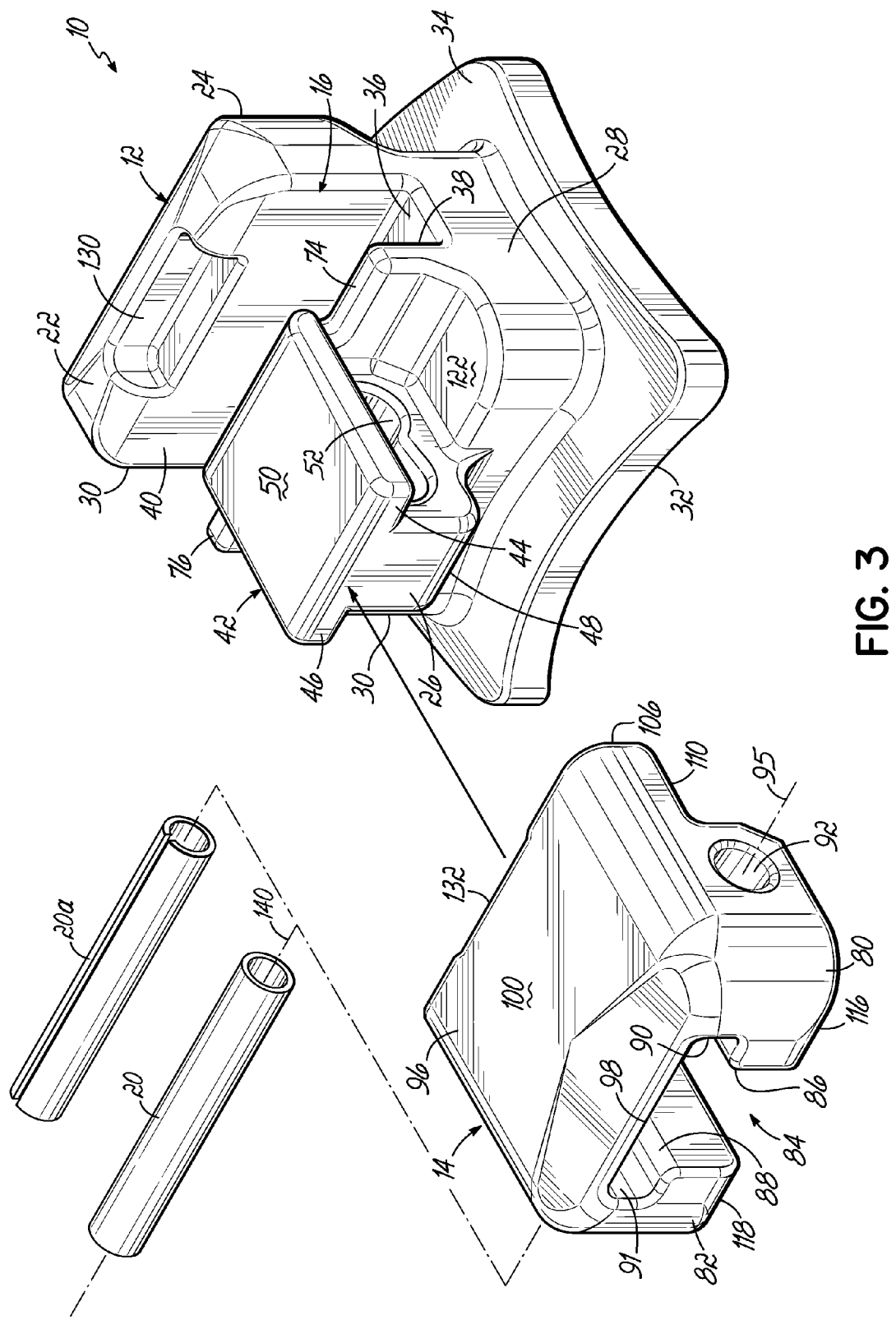
FIG. 3 is an exploded perspective view of the orthodontic bracket shown in FIG. 2.

When mounted to the labial surface of a tooth T carried on the patient's lower jaw (labeled in FIG. 1) and with reference specifically to FIG. 3, the bracket body 12 has a labial side 22, an occlusal side 24, a gingival side 26, a mesial side 28, a distal side 30, and a lingual side 32. The lingual side 32 of the bracket body 12 is configured to be secured to the tooth in any conventional manner, such as for example, by an appropriate orthodontic cement or adhesive or by a band around an adjacent tooth. In one embodiment shown in FIGS. 1-3, the lingual side 32 may further be provided with a pad 34 defining a bonding base that is secured to the surface of the tooth T. The pad 34 may be coupled to the bracket body 12 as a separate piece or element, or alternatively, the pad 34 may be integrally formed with the bracket body 12. Further, the pad 34 may be specifically shaped to fit on the surface of a particular tooth surface. The pad 34 may therefore have a multitude of configurations different from that shown in FIGS. 1-3. It will be appreciated that embodiments of the present invention are not limited to any particular configuration of the pad 34.

With reference to FIGS. 1 and 2, the bracket body 12 includes a base surface 36 and a pair of opposed slot surfaces 38, 40 projecting labially from the base surface 36 that collectively define the archwire slot 16, which may extend in a mesial-distal direction from mesial side 28 to distal side 30. The base surface 36 and slot surfaces 38, 40 are substantially encapsulated or embedded within the material of the bracket body 12. While not being limited thereto, the bracket body 12 and/or ligating slide 14 may be made of a ceramic, such as, that described in commonly owned U.S. Pat. No. 8,585,398, issued Nov. 19, 2013, and U.S. Publication No. 2010/0173256, published Jul. 8, 2010, the disclosures of which are incorporated by reference herein in their entireties.

As shown in FIG. 3, in one embodiment, the bracket body 12 further includes a slide support portion 42 configured to receive the ligating slide 14 thereon. The slide support portion 42 may generally project labially from or be oriented generally perpendicular to the pad 34. The slide support portion 42 may also extend generally perpendicular to the archwire slot 16. The slide support portion 42 may terminate on its labial-most portion in a support surface 50 to slidably engage the ligating slide 14 over at least a portion of its translational motion from the opened position to the closed position. In a labial application (shown in FIG. 1), the support surface 50 is positioned gingivally of the archwire slot 16 and extends lengthwise in a generally occlusal-gingival direction.

Figure 4:
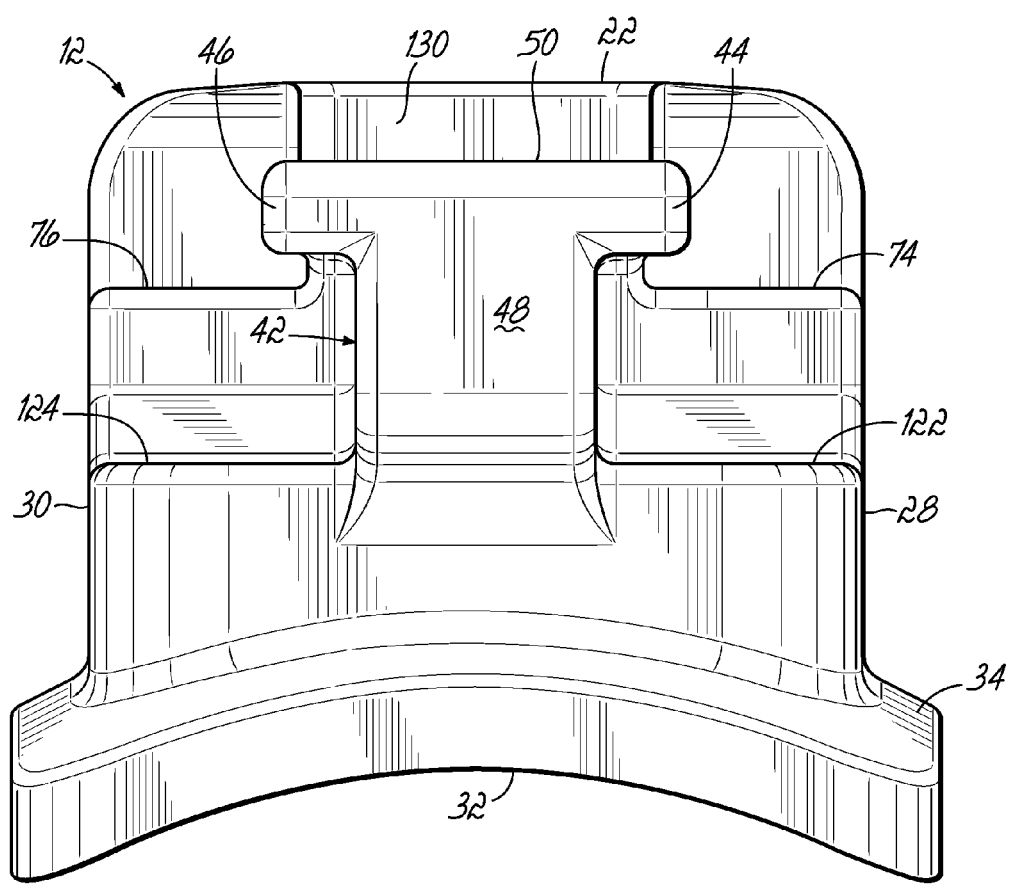
FIG. 4 is a front elevation view of the orthodontic bracket body shown in FIG. 3.
Figure 5:
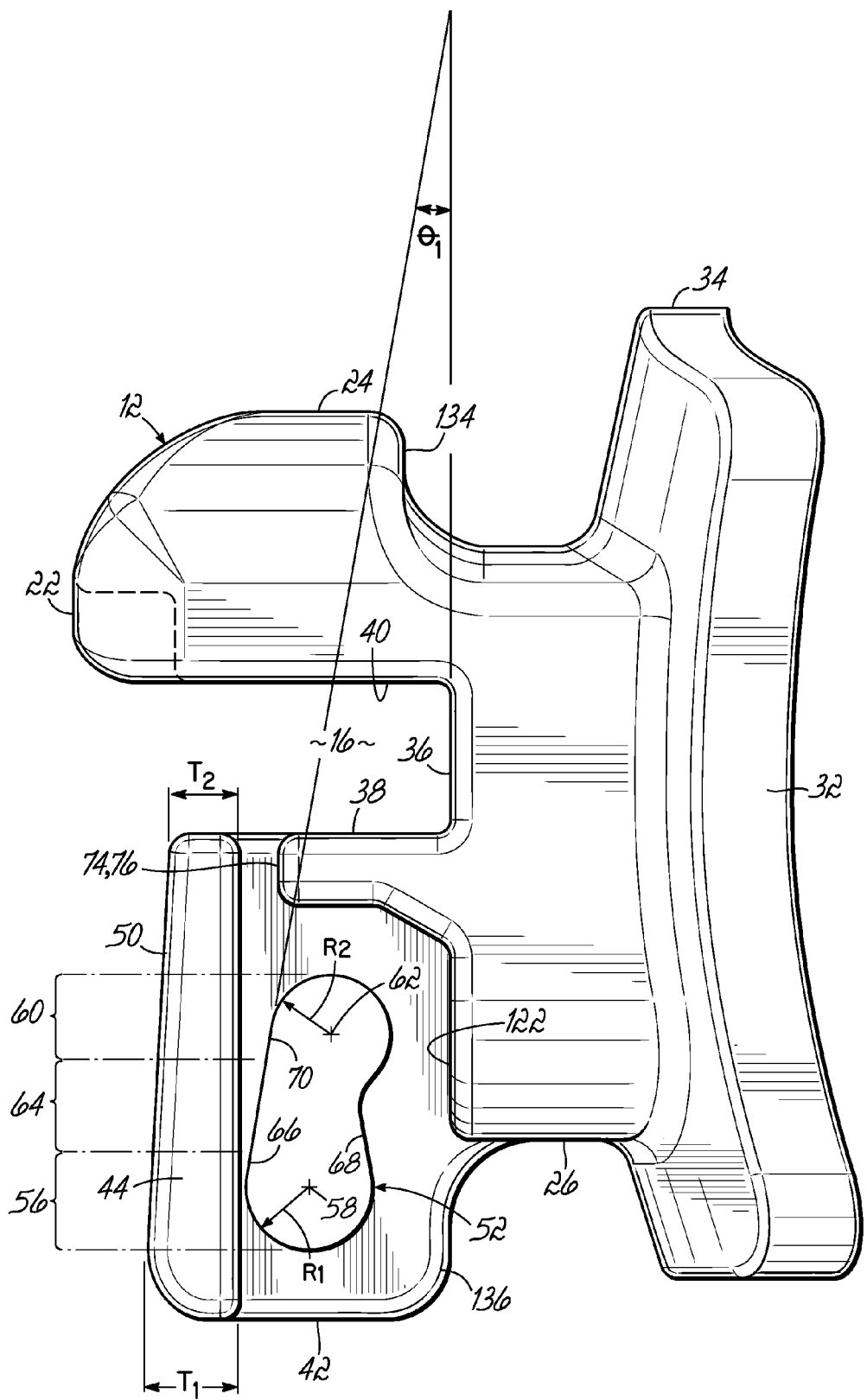
FIG. 5 is a side elevation view of the orthodontic bracket body shown in FIG. 3.

With reference now to FIGS. 4 and 5, in one embodiment, the slide support portion 42 has a generally T-shaped configuration (shown best in FIG. 4) with opposing mesial and distal projections or wings 44, 46 extending from a central portion 48. In the configuration shown, the mesial and distal wings 44, 46 may taper in thickness in the occlusal-gingival direction (shown best in FIGS. 5 and 5A). With specific regard to the tapered wings 44, 46 shown, each wing 44, 46 may uniformly decrease in thickness from the gingival-most edge to the occlusal-most edge of the slide support portion 42. By way of example only, the thickness T1 of each wing 44, 46 at the gingival-most edge of the slide support portion 42 may be about 0.015 inches, and the thickness T2 of each wing 44, 46 at the occlusal-most edge of the slide support portion 42 may be about 0.010 inches. Thus, the taper may be about 30% in thickness over the gingival-occlusal length of the mesial and distal wings 44, 46. In general, the change in thickness of each of the wings 44, 46 may allow the slide 14 to move outwardly (e.g., labially) relative to the base surface 36 of the archwire slot 16 when the slide 14 is in the closed position shown in FIG. 1, as is described in more detail below.

With continued reference to FIG. 5, in one embodiment, the support surface 50 may be angled with respect to the base surface 36. In particular, the support surface 50 may be oriented so as to be tilted toward the archwire slot 16 with the thinnest portion of the wings 44, 46 nearest the archwire slot 16. It will be appreciated that the wings 44, 46 may taper in the opposite direction of that shown and provide the functionality described below.

Figure 5A:
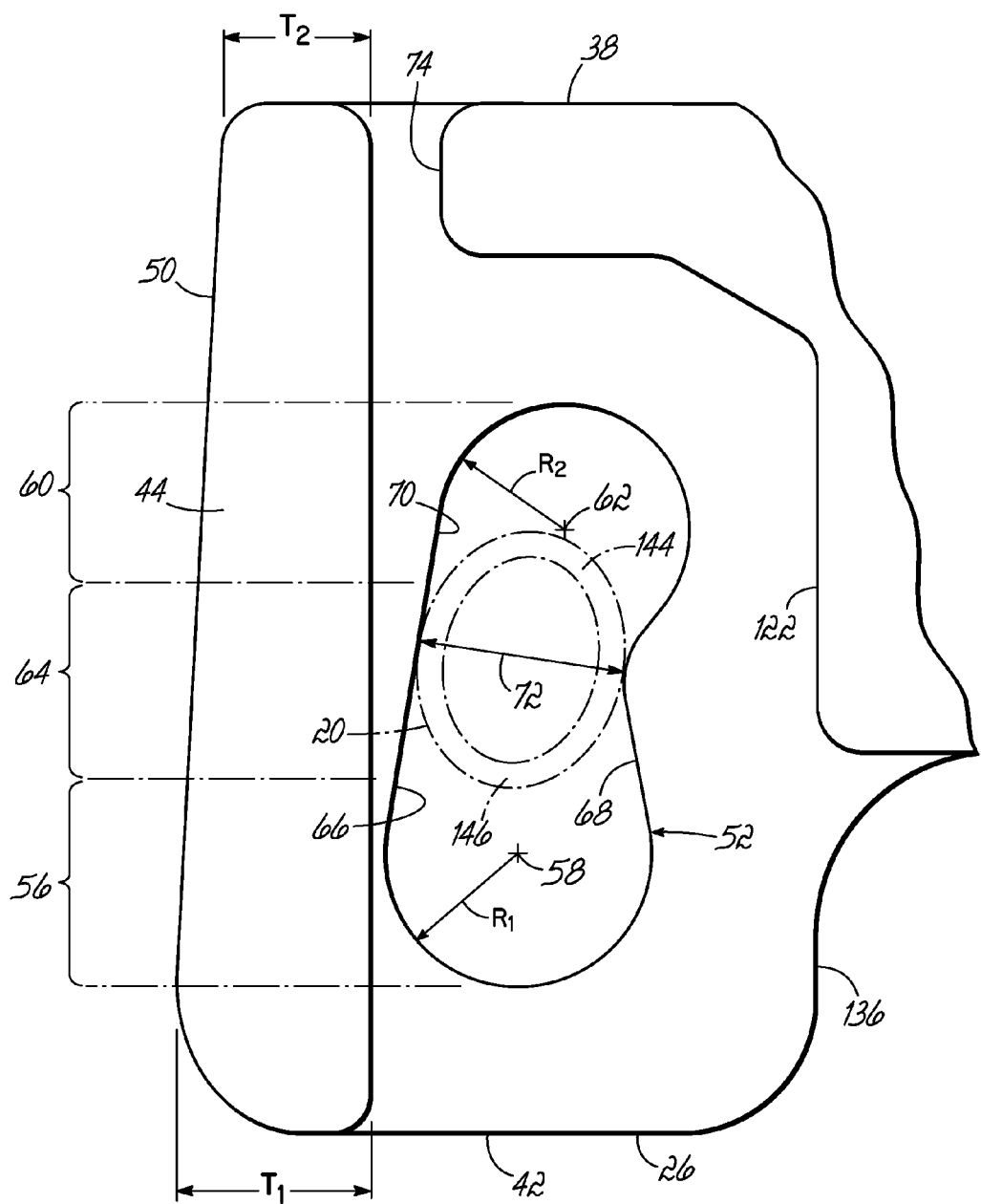
FIG. 5A is an enlarged view of the encircled area 5A of FIG. 5.

Also shown in FIGS. 5 and 5A, the slide support portion 42 includes an aperture 52 formed as a through bore in the mesial-distal direction. The aperture 52 may be positioned so that the longitudinal axis of the resilient member 20 extends generally parallel with the archwire slot 16 and in the mesial-distal direction. In one embodiment, the aperture 52 is a generally asymmetrical bore about a plane that is perpendicular to the direction of slide motion as indicated by arrow 54 shown in FIG. 2. The aperture 52 may be described as having an irregular configuration.

As will be described in detail below, the aperture 52 is configured to slidably engage the resilient member 20 so as to bias the ligating slide 14 in a particular direction when the ligating slide 14 is in the closed position. For example, when the slide 14 is in the closed position, as is shown in FIG. 1, the aperture 52, in conjunction with the resilient member 20 and the slide 14, produces a net force on the slide 14 to hold it in the closed position. This net force must then be overcome, in addition to other forces described below, before the slide 14 can be moved away from the closed position or, according to FIG. 1, in the gingival direction or toward the opened position. The net force maintains the slide 14 in a fixed, more stable position relative to the bracket body 12 thereby maintaining a more consistent labial-lingual archwire slot dimension. Advantageously, stack up tolerances in the labial-lingual direction are reduced or eliminated.

As shown in FIGS. 5 and 5A, the aperture 52 may include a first lobe portion 56 proximate the gingival side 26. By way of example only, the first lobe portion 56 may define a generally circular perimeter along a portion of the aperture 52. The lobe portion 56 may be defined by an axis 58 and a radius R1. The aperture 52 may further include a second lobe portion 60 nearest the archwire slot 16, that is, positioned occlusally of the first lobe portion 56. Similar to the first lobe portion 56, the second lobe portion 60 may be defined by a generally circular perimeter having an axis 62 and a radius R2.

In one embodiment, the aperture 52 may include a central portion 64 positioned between and connecting the first lobe portion 56 and the second lobe portion 60. The central portion 64 may include a first segment 66 that is tangent to the first lobe portion 56 and that is also tangent to the second lobe portion 60. The first lobe portion 56, the second lobe portion 60, and the first segment 66 may generally define a slide track 70 for the resilient member 20. As is generally indicated in FIG. 5, a projection of the slide track 70 may form an acute angle 81 with the base surface 36 of the archwire slot 16. The slide track 70 may be parallel with the support surface 50. Or, the slide track 70 may be oriented at a slightly smaller angle with a plane including the base surface 36 as compared to an angle between the support surface 50 and a plane including the base surface 36.

In addition, the central portion 64 may include a second segment 68 opposite the first segment 66. The second segment 68 may be tangent to the first lobe portion 56, but may extend in a direction such that an extension of the second segment 68 would intersect (rather than be tangent to) the second lobe portion 60. By further extending the second segment 68, it intersects an extension of the first segment 66. The angle formed between the first and second segments 66, 68 may be equal to or less than about 60° and may depend on a particular tooth onto which the bracket 10 is to be affixed. By way of example, the second segment 68 may be angled at between about 10° and about 30° with respect to the first segment 66, and by way of further example, the second segment 68 may be angled from about 19° to about 21° with respect to the first segment 66.

With continued reference to FIGS. 5 and 5A, in one embodiment, the orientation of the first segment 66 and the second segment 68 of the central portion 64 forms a restriction or pinch point 72 between the first lobe portion 56 and the second lobe portion 60. The pinch point 72 is generally a narrowing of the aperture 52 between the first and second lobe portions 56, 60. This may include narrowing of the aperture 52 to a dimension that is less than each of the largest height (or labial-lingual) dimensions for the first and second lobe portions 56, 60. By way of example only and not limitation, where each of the first and second lobe portions 56, 60 generally define circular bores having radii R1 and R2, respectively, the pinch point 72 may be measured as a perpendicular distance between the first segment 66 and the nearest opposing portion of the central portion 64. This perpendicular distance may be less than the diameter of the first lobe portion 56 or less than the diameter of the second lobe portion 60 or less than each of the diameters of the first lobe portion 56 and the second lobe portion 60. Further, this dimension may be at least 5% less or in the range of about 10% to about 20% less than either diameter of the first or second lobe portions 56, 60. In one embodiment, the radius R2 is less than the radius R1 and the pinch point 72 is sized to be less than twice R2. By way of example and not limitation, radius R2 may be about 5% to about 15% less than radius R1. In an exemplary embodiment, the radius R1 may be about 0.010 inches and the radius R2 may be about 0.009 inches and the pinch point 72 may measure about 0.017 inches.

As set forth above, the aperture 52 may be asymmetric. The asymmetry may be a result of the pinch point 72 being offset from a halfway point of the overall length of the aperture 52. As shown in FIGS. 5 and 5A, pinch point 72 is shifted toward the second lobe portion 60. Based on this shift alone, the aperture 52 is asymmetric about a plane that forms a perpendicular bisector of the overall length of the aperture 52. In addition, in embodiments where the first and second lobe portions 56, 60 are generally circular, the difference in corresponding radius dimension also produces asymmetry in the aperture 52. The asymmetry in the aperture 52 may produce a distinctive tactile response in the movement of the slide 14. In particular, as set forth in detail below, the asymmetry in the aperture 52 may provide the clinician with a distinctive "click" or "snap" to indicate that the slide 14 is in the closed position.

With continued reference to FIGS. 4 and 5, in one embodiment of the invention, the bracket body 12 has at least one shoulder 74 oriented at an angle relative to the slide track 70. In the embodiment shown, the bracket body 12 has mesial and distal shoulders 74, 76 that extend in a generally mesial or distal direction from the central portion 48 and adjacent the archwire slot 16. By way of example, each of the shoulders 74, 76 intersects the archwire slot 16 at the opposed slot surface 38. It will be appreciated, however, that embodiments are not limited to the shoulders 74, 76 in the configuration shown.

With reference to FIGS. 4 and 5, the mesial shoulder 74 and distal shoulder 76 are angled relative to the slide track 70 and generally face in the labial direction. The relative orientation of one or both of the shoulders 74, 76 may be similar to or the same as that of the base surface 36. For example, each shoulder 74, 76 is generally parallel with the base surface 36 and defines a height H1 (labeled in FIG. 9D) above the base surface 36. As is shown in FIG. 1, one or more of the shoulders 74, 76 may form a contact surface against which the slide 14 resides when it is in the closed position and not actively ligating an archwire in the archwire slot 16, which is described in detail below.

With reference to FIGS. 1-4, the bracket body 12 further includes a tool recess 130 formed labially of the archwire slot 16 and extending in a direction generally toward the occlusal side 24. The tool recess 130 provides a depression or recessed region that is at least partially closed off from the occlusal side 24 of the bracket body 12 when the slide 14 is in the closed position. The tool recess 130 is configured to receive a tool (not shown) for opening the ligating slide 14. The tool, such as a Spin Tek™ tool from Ormco Corporation or a similar tool may be inserted into the tool recess 130 in a direction that is generally aligned with the archwire slot 16. Rotation of the tool by 90° from the direction of insertion leverages the tool against the bracket body 12 at or near the slot surface 40 and pushes the slide 14 toward the opened position.

Figure 8:
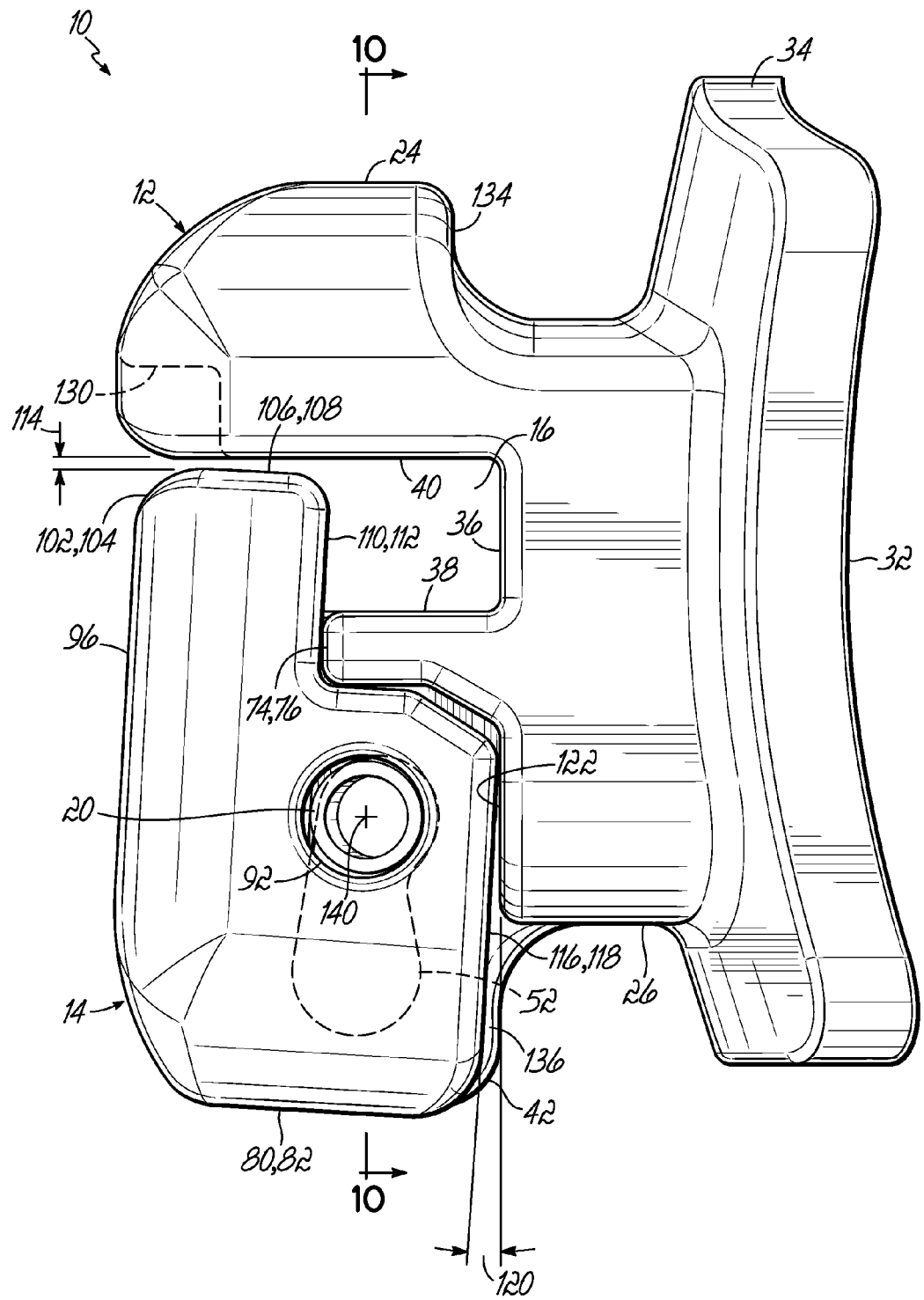
FIG. 8 is a side elevation view of the orthodontic bracket shown in FIG. 1.

Additionally, in one embodiment, and with reference to FIG. 8, the bracket body 12 may include an occlusal tie wing 134 and a gingival tie wing 136. It will be appreciated that the opposing tie wings 134, 136 may provide a region in which the clinician may engage a ligature, for example, to provide additional pressure on the slide 14 to maintain it against the bracket body 12 and in the closed position during treatment.

Figure 6:
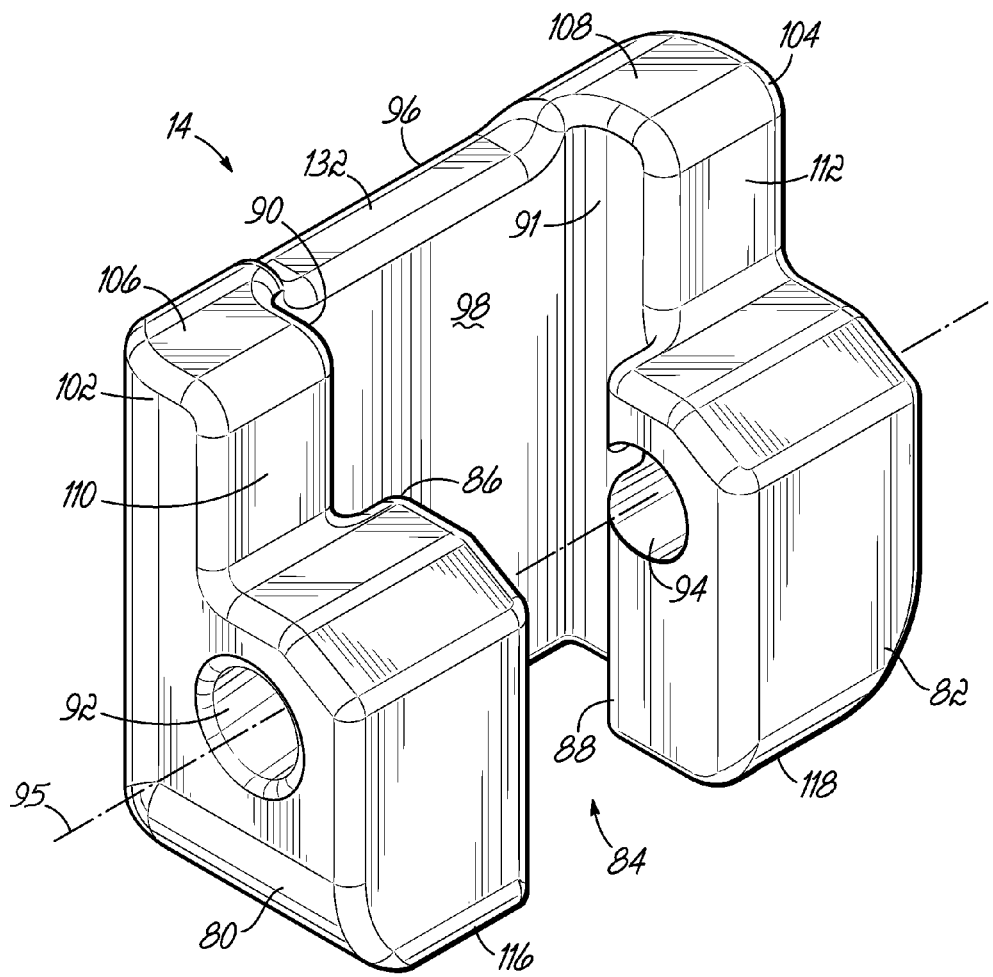
FIG. 6 is a perspective view of the slide member shown in FIG. 3.
Figure 7:
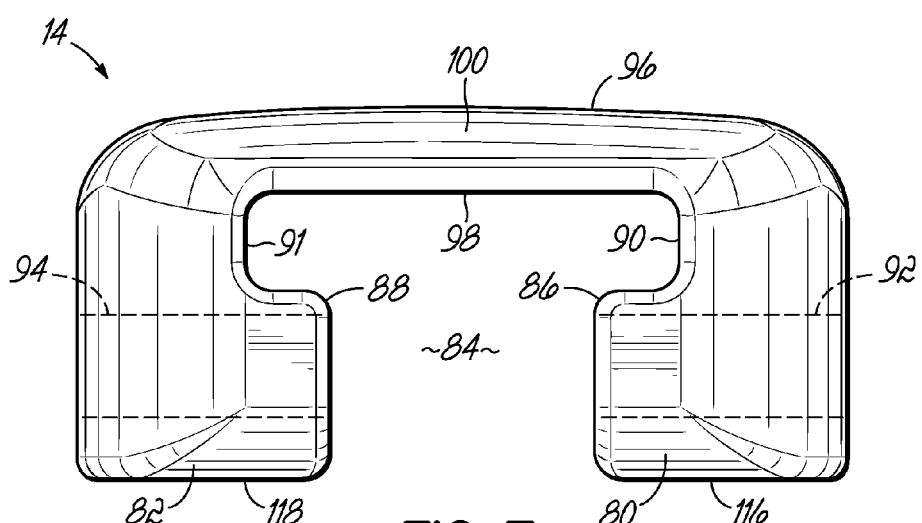
FIG. 7 is a rear elevation view of the slide member shown in FIG. 3.

With reference to FIGS. 3, 6, and 7, the ligating slide 14 is generally a U-shaped configuration (depicted best in FIG. 7). The ligating slide 14 includes a first leg or mesial portion 80 and second leg or a distal portion 82 that generally define a slide channel 84 therebetween. The slide channel 84 is dimensioned to slidably cooperate with the slide support portion 42.

In this regard, the mesial and distal portions 80, 82 may have shoulders 86, 88 projecting inwardly and that generally correspond in shape to the central portion 48. The shoulders 86, 88 may define corresponding recess regions 90, 91 that are configured to slidably receive the wings 44, 46. The recess regions 90, 91 may generally be uniform in dimension along their gingival-occlusal length. In other words, the recess regions 90, 91 may not be tapered. It will be appreciated that embodiments of the present invention are not limited to uniform recess regions 90, 91 and tapered wings 44, 46 as the reverse construction, namely, tapered recess regions and uniform wings, or a combination of tapered recess regions and tapered wings is possible and within the scope of the present invention. As shown, the slide channel 84 may therefore have a T-shaped configuration that compliments or corresponds to the shape of the support portion 42 of the bracket body 12.

With reference to FIGS. 3 and 6, each of the mesial and distal portions 80, 82 includes at least one through-bore that receives the resilient member 20. As shown, the mesial portion 80 includes a mesial through-bore 92 and the distal portion 82 includes a distal through-bore 94. The bores 92, 94 share a common axis 95. As shown, the common axis 95 is positioned lingually of a plane that includes the labial edge of the archwire slot 16 as determined by the ligating slide 14 in the closed position. As will be described below, this orientation may facilitate elastic deformation of the resilient member 20 as the ligating slide 14 pivots. It will be appreciated that the bore 92 and the bore 94 may be sized to be slightly larger than the diameter or equivalent dimension of the resilient member 20. By way of example, the bores 92, 94 may be about 0.002 inches larger in dimension than the largest corresponding outer dimension of the resilient member 20. By way of further example, the bores 92, 94 may measure from about 10% to about 20% larger than the corresponding outer dimension of the resilient member 20. Alternatively, the bores 92, 94 may be equal to or smaller than the outside dimension (e.g., outside diameter) of the member 20. For example, the bores 92, 94 may be about 0.0002 inch smaller in inside diameter than the outside diameter of the member 20. In this case, the member 20 may be press fit into each of the bores 92 and 94.

As shown in FIGS. 6 and 7, the mesial and distal portions 80, 82 extend from a cover portion 96 that defines a sliding surface 98 and an outer surface 100. In the exemplary embodiment shown, the outer surface 100 forms the labial-most surface of the ligating slide 14. In one embodiment, the ligating slide 14 includes a mesial ligating portion 102 and a distal ligating portion 104 formed along the occlusal-most portion of each of the mesial and distal portions 80 and 82, respectively. In the exemplary embodiment shown, the mesial and distal ligating portions 102, 104 each include a corresponding leading surface 106, 108 and a corresponding lingually-facing surface 110, 112.

When the ligating slide 14 is in the closed position, as is shown in FIG. 8, the lingually-facing surfaces 110, 112 oppose the base surface 36 and thereby form a fourth side of the archwire slot 16 and define a lumen that retains the archwire 18 therein. Specifically, the surfaces 110, 112 form the labial boundary of the archwire slot 16 to capture an archwire in the archwire slot 16 during orthodontic treatment. In one embodiment, the lingually-facing surfaces 110, 112 abut the mesial and distal shoulders 74, 76 when the ligating slide 14 is in the closed position.

In addition, in one embodiment, the ligating slide 14 includes a tool recess 132 in the cover portion 96 between the mesial and distal ligating portions 102, 104. The tool recess 132 may be positioned opposite the recess 130 (shown in FIG. 1) so that the tool recesses 130 and 132 collectively receive a tool for opening the ligating slide 14. Specifically, a tool (not shown) may be inserted between the ligating slide 14 and the bracket body 12 within each of recesses 130 and 132. Full rotation of the tool to 90° from its orientation upon insertion into the tool recesses 130 and 132 may facilitate movement of the ligating slide 14 from the closed position toward the opened position.

As introduced above, in one embodiment, and as illustrated in FIG. 3, the resilient member 20 may be generally tubular having a circular cross section. The cross section may be continuous, that is, the tubular resilient member 20 may be without slots or other discontinuities in its sidewall. In this regard, and unlike a slotted tubular spring pin, the perimeter of the resilient member 20 is generally maintained when the resilient member 20 is elastically deformed. Alternatively, as shown in FIG. 3, a resilient member 20a may have a single slot through its sidewall that extends lengthwise generally parallel with the longitudinal axis. The resilient member 20a may be composed of a similar material as the resilient member 20, described below, and is described in commonly owned U.S. Pat. No. 8,033,824, which is incorporated by reference herein in its entirety. Unless specifically noted herein, reference to the "resilient member 20" is a reference to either of the resilient member 20 or the resilient member 20a, each shown in FIG. 3.

The resilient member 20 may be dimensioned to fit within the bores 92, 94 and through the aperture 52. In an exemplary embodiment, the resilient member 20 may be composed of Nickel Titanium (NiTi) superelastic material. By way of example, one NiTi composition includes about 55 wt. % nickel (Ni), and about 45 wt. % titanium (Ti) with minor amounts of impurities and is available from NDC of Fremont, Calif. The mechanical properties of the NiTi alloy may include an ultimate tensile strength of greater than about 155 ksi, an upper plateau of greater than about 55 ksi, and a lower plateau of greater than about 25 ksi. The dimensions of the resilient member 20 may vary depending on the size of the bracket itself. In one embodiment, the resilient member 20 is a right circular, hollow cylinder having an axis 140 and a diameter of about 0.016 inches and being from about 0.50 inches to about 0.125 inches in length. The wall thickness may measure from about 0.001 inches to about 0.004 inches, and may preferably be about 0.002 inches to about 0.003 inches.

In view of the above, and with reference to FIG. 3, the slide 14 is assembled with the bracket body 12 by a sliding motion from beyond the gingival side 26 of the bracket body 12 in a direction toward the archwire slot 16. When the ligating slide 14 is assembled with the bracket body 12, the sliding surface 98 slidably engages the support surface 50 of the slide support portion 42 (shown best in FIG. 3) over at least a portion thereof.

The T-shaped configuration of the slide support portion 42, in cooperation with the inversely shaped configuration of the slide channel 84, may inhibit or eliminate instances where the slide 14 accidentally disengages from the bracket body 12 in an outward or labial direction in the event that the resilient member 20 fails. By this construction, the resilient member 20 may provide a mechanism for securing the ligating slide 14 to the bracket body 12 in the opened position and in all of the closed positions. In one embodiment, the resilient member 20 cooperates with the bracket body 12, and more particularly extends through the aperture 52, to secure the slide 14 to the bracket body 12 in each of the opened and the closed positions.

With reference to FIGS. 3 and 6, after the ligating slide 14 is positioned on the bracket body 12, the resilient member 20 is inserted. As shown in FIG. 3, the resilient member 20 is positioned in through-bore 94 and through the aperture 52 and into the opposing bore 92 along axis 95. During assembly, the resilient member 20 may be press fit or slip fit into bores 92, 94, and/or may be secured therein to prevent relative movement therebetween using various processes including staking, tack welding, laser welding, adhesives, or other suitable methods.

Once assembled, as is shown in FIG. 8, in one embodiment, the lingually-facing surfaces 110, 112 do not extend the full width or perpendicular distance of the archwire slot 16. In this regard, the occlusally oriented leading surfaces 106, 108 may not abut the opposing surfaces of the bracket body 12. For example, surfaces 106, 108 do not contact the slot surface 40. Accordingly, there remains a gap 114 between the bracket body 12 and the ligating slide 14 at this location. The gap 114 may be intentional and necessary to assure that the ligating slide 14 is consistently positioned in contact with one or both shoulders 74, 76 relative to the base surface 36 under the load imposed by the resilient member 20.

By building in a gap at this location, contact between the lingually-facing surfaces 110, 112 of the ligating slide 14 and the shoulders 74, 76 of the bracket body 12 during treatment is more probable or likely. Reducing the number of other points of contact between the ligating slide 14 and the bracket body 12 increases the likelihood that the ligating slide 14 is more consistently positioned relative to the bracket body 12. Specifically, limiting contact with other locations or providing a built-in gap at other locations increases the probability of consistent contact between the lingually-facing surfaces 110, 112 and the shoulders 74, 76. By way of example, the gap 114 may be at least about 0.001 inches, and by way of further example, the gap 114 may measure in the range of about 0.001 inches to about 0.005 inches. It will be appreciated, however, that the maximum dimension of the gap 114 may only be limited by the minimum extension of the ligating portions 102, 104 required to capture the archwire 18 within the archwire slot 16.

With further reference to FIGS. 7 and 8, another gap or clearance may be built in between the slide 14 and the bracket body 12. In one embodiment, each of the mesial and distal portions 80, 82 is defined by surfaces 116 and 118 that oppose the bracket body 12 but do not slidably engage or contact the bracket body 12 when the ligating slide 14 is in the closed position, as shown. In this regard, there is a built-in gap 120 between the ligating slide 14 and the bracket body 12. Specifically, between the surface 116 and the bracket body 12 at mesial shoulder 122 and between the surface 118 and the bracket body 12 at distal shoulder 124 (shown in FIG. 4). By way of example, and not limitation, the gap 120 may be similarly dimensioned as the gap 114 between the surfaces 106, 108 and the slot surface 40, as described above. Specifically, the gap 120 may measure at least about 0.001 inches, and by way of further example, may measure from about 0.001 inches to about 0.005 inches when the ligating slide 14 is in the closed position.

In one embodiment, the slide 14 contacts the bracket body 12 along only two surfaces. One contact surface is the support surface 50 and the other surface may be one of the shoulders 74 or 76. Where both shoulders 74, 76 contact the slide 14, there are only three surfaces of contact between the slide 14 and the bracket body 12. By providing only a limited number of contact points, the position of the slide 14 relative to the bracket body 12 is more consistent.

As described above, the ligating slide 14 may have multiple closed positions; the resilient member 20 may bias the ligating slide 14 in each closed position. By way of example, the resilient member 20 may bias the slide 14 in the direction of translational motion of the slide 14. With regard to the bias imposed by the resilient member 20 on the ligating slide 14, embodiments of the present invention may include a biased ligating slide similar to that shown and described in either of commonly owned U.S. Publication No. 2014/0127638, filed on Nov. 5, 2013, and U.S. application Ser. No. 14/205,674, filed Mar. 12, 2014, the disclosures of which are incorporated by reference herein in their entireties.

Biasing the slide 14 may also include biasing in a direction toward the archwire slot 16. Because the ligating slide 14 may be biased by resilient member 20, the tolerance variations in the ligating slide 14 are no longer relevant in setting the depth of the archwire slot 16 in the generally labial-lingual direction. This is because, regardless of the magnitude of tolerance, the ligating slide 14 may contact the shoulders 74, 76 of the bracket body 12.

During orthodontic treatment with an archwire that has a labial-lingual dimension that is equal to or less than the dimension between the base surface 36 and the lingually-facing surfaces 110, 112, the ligating slide 14 may contact the mesial and distal shoulder 74, 76 and be biased while in that position. Thus, the tolerance variation that must still be considered and monitored during manufacturing is the tolerance in the positioning of the shoulders 74, 76 relative to the base surface 36 of the archwire slot 16. Advantageously, this reduces the number of tolerances that stack up to ultimately determine the depth of the archwire slot 16 in the generally labial-lingual direction and thereby provides a more consistent fit between the lumen, created by the bracket body 12 and the ligating slide 14, and the archwire 18. It is believed that rotational control of the teeth may be more consistently maintained and predictable during orthodontic treatment.

Specifically, during use, and as is illustrated in the sequence of FIGS. 9A-9D, when the ligating slide 14 is in the opened position, the resilient member 20 may be positioned within the first lobe portion 56 of the aperture 52. The common axis 95 of each of the bores 92, 94 may be aligned with the axis 58 of the first lobe portion 56. The axis 140 of the resilient member 20 may also be aligned with the axis 58 depending on the cross-sectional dimensions of the resilient member 20. Generally, in this position, and where each of the first lobe portion 56 and bores 92, 94 are generally larger in dimension than the resilient member 20, the resilient member 20 is in a relaxed, undeformed state and may not bias the ligating slide 14 in any given direction. However, the resilient member 20 may resist external forces acting on the slide 14 in a direction indicated by arrow 142 in FIG. 9A.

In this regard, when an archwire is removed from the archwire slot 16 and before a new archwire is inserted into the archwire slot 16, the ligating slide 14 may resist being inadvertently pushed to a closed position from the opened position. Because the central portion 64 includes the segment 68, which provides a gradually decreasing clearance dimension that is less than the outside diameter of the resilient member 20, the central portion 64 interferes with movement of the resilient member 20 in the direction indicated by arrow 142. Advantageously, interference between the segment 68 and the resilient member 20 limits the movement distance of the slide 14 before more significant force is required. The slide 14 therefore resists unintentional forces and remains substantially in the opened position until intentionally closed. It will be appreciated that a clinician, after positioning the slide 14 in the opened position, may remove an existing archwire from the archwire slot 16 and insert another archwire into the archwire slot 16 without concern that the ligating slide 14 will inadvertently move toward the closed position.

Further in this regard, the interaction between the member 20 and the aperture 52 may require intentional application of force to move the ligating slide 14 to the closed position. A minimum threshold force may therefore be required on the slide 14 to move it toward the closed position. In one embodiment, the minimum threshold force is greater than the sliding weight of the slide 14. In this embodiment, only when the force on the slide 14 exceeds the minimum threshold force does the resilient member 20 move toward the closed position. Forces on the slide 14 that exceed the minimum threshold force cause the resilient member 20 to elastically deform. Elastic deformation of the resilient member 20 is dictated by the shape of the central portion 64 of the aperture 52. In this regard, elastic deformation of member 20 may be localized to a region of contact with the aperture 52. By elastic deformation, the strain produced in the resilient member 20 is fully recovered, and the member 20 reverts to its original shape, upon removal of the deforming force.

Figure 9A:
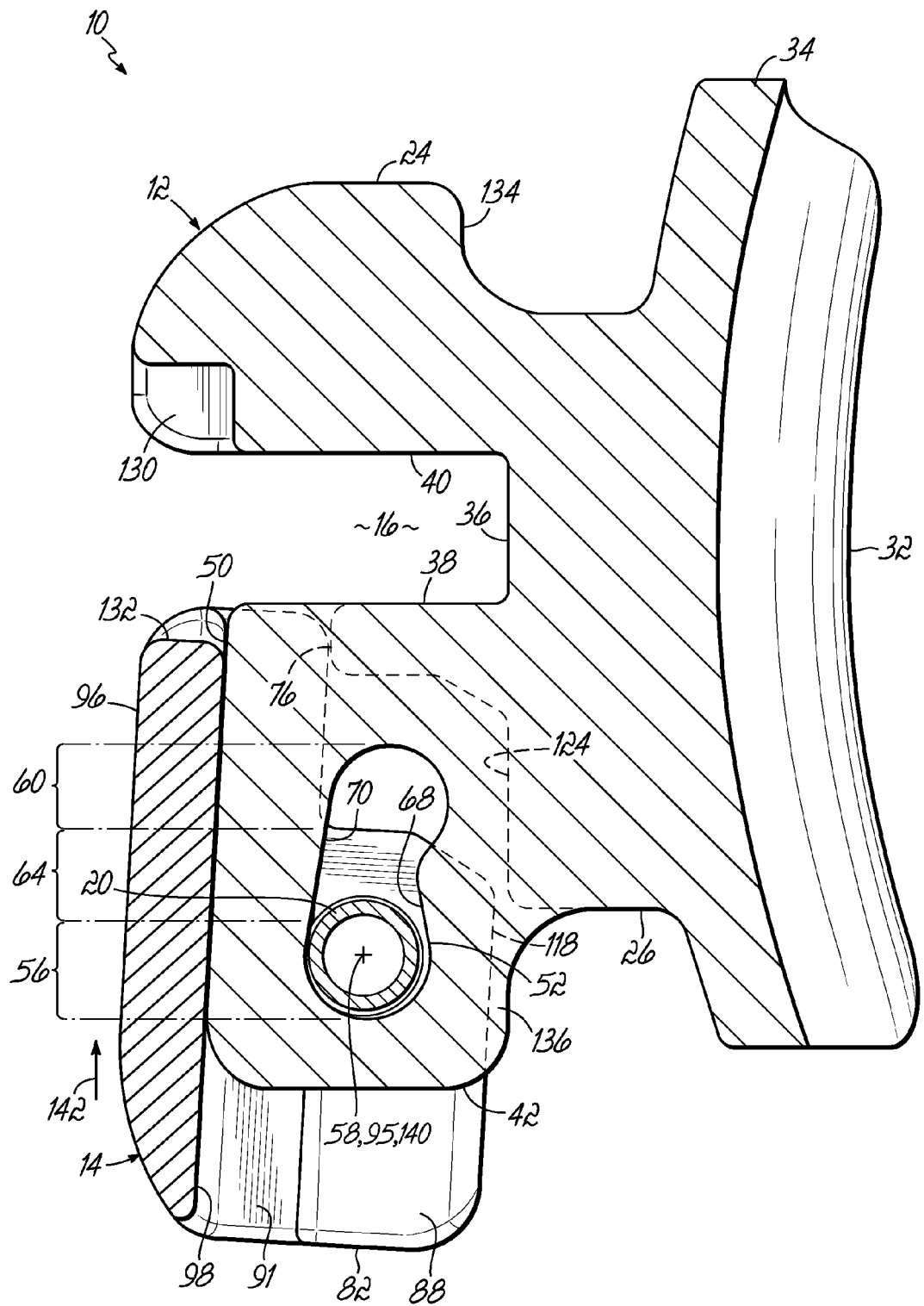
FIG. 9A is a cross-sectional view of the orthodontic bracket taken along section line 9A-9A of FIG. 2, depicting the slide member in the opened position.
Figure 9B:
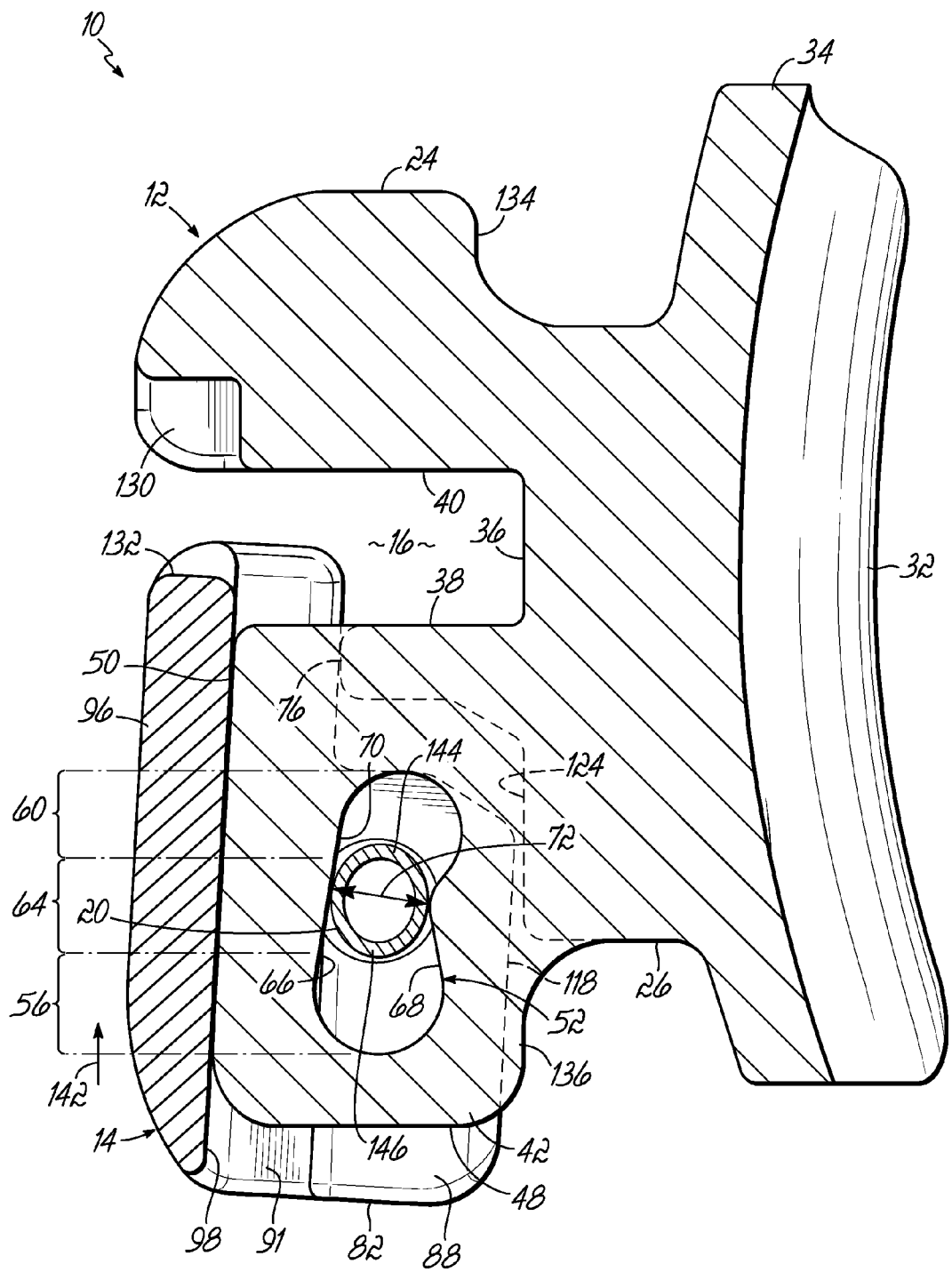
FIG. 9B is a cross-sectional view of the orthodontic bracket taken along section line 9A-9A of FIG. 2, depicting the slide member in a position between the closed position of FIG. 1 and the opened position shown in FIG. 2.

FIG. 9B depicts an exemplary embodiment in which a force on the slide 14 exceeds the minimum threshold force required to move the slide 14 toward the closed position. Where the force on the slide 14 is sufficient to cause elastic deformation of the resilient member 20, the slide 14 may be moved toward the closed position and, in particular, cause a central portion of the resilient member 20 that is in contact with the aperture 52 to elastically deform due to the applied load on the ligating slide 14. It will be appreciated that depending on the configuration of the second segment 68, a gradually increasing force may be required to continuously move the slide 14 along the slide track 70 toward the closed position. The rate at which the force is required to increase is dictated by the shape of the central portion 64 and the properties of the resilient member 20.

For the exemplary embodiment shown in FIG. 9B, the second segment 68 is a generally planar surface and is believed to require a generally linear increase in force on the slide 14, at least over a portion of the opening movement, to deform the resilient member 20 as shown. The resilient member 20 may deform in a manner which allows it to conform to the shape defined by the distances between the region of contact between the resilient member 20 and the first segment 66 and the region of contact between the resilient member 20 and the second segment 68. As shown, the resilient member 20 may elastically deform by a change in the cross-sectional profile of the member 20. This may include a change to a roughly egg-shaped cross section in the region of contact between the resilient member 20 and the aperture 52. Portions of the resilient member 20 outside of the aperture 52 may not significantly elastically deform and thus retain their original cross-sectional profile. For example, the portions of the resilient member 20 in the bores 92, 94 may remain substantially circular. Thus, elastic deformation of the resilient member 20 may be localized to discrete regions of the resilient member 20 in sliding contact with the aperture 52. It will be appreciated that embodiments of the invention are not limited to any particular form or shape of the resilient member 20. In addition to elastic deformation about the cross-section of the resilient member 20 in contact with the aperture 52, the resilient member 20 may elastically deform along its longitudinal axis in response to the load applied to the ligating slide 14. That is, when the ligating slide 14 is pushed toward the closed position and the resilient member 20 encounters the second segment 68, the resilient member 20 may elastically deform by bowing along its longitudinal axis 140. By way of example, each of the ends of the resilient member 20 in the mesial and distal through-bores 92, 94 may be positioned closer to the archwire slot 16 than the central portion of the resilient member 20 in contact with the aperture 52. The resilient member 20 may therefore bend along its axis during movement of the ligating slide 14.

Figure 9C:
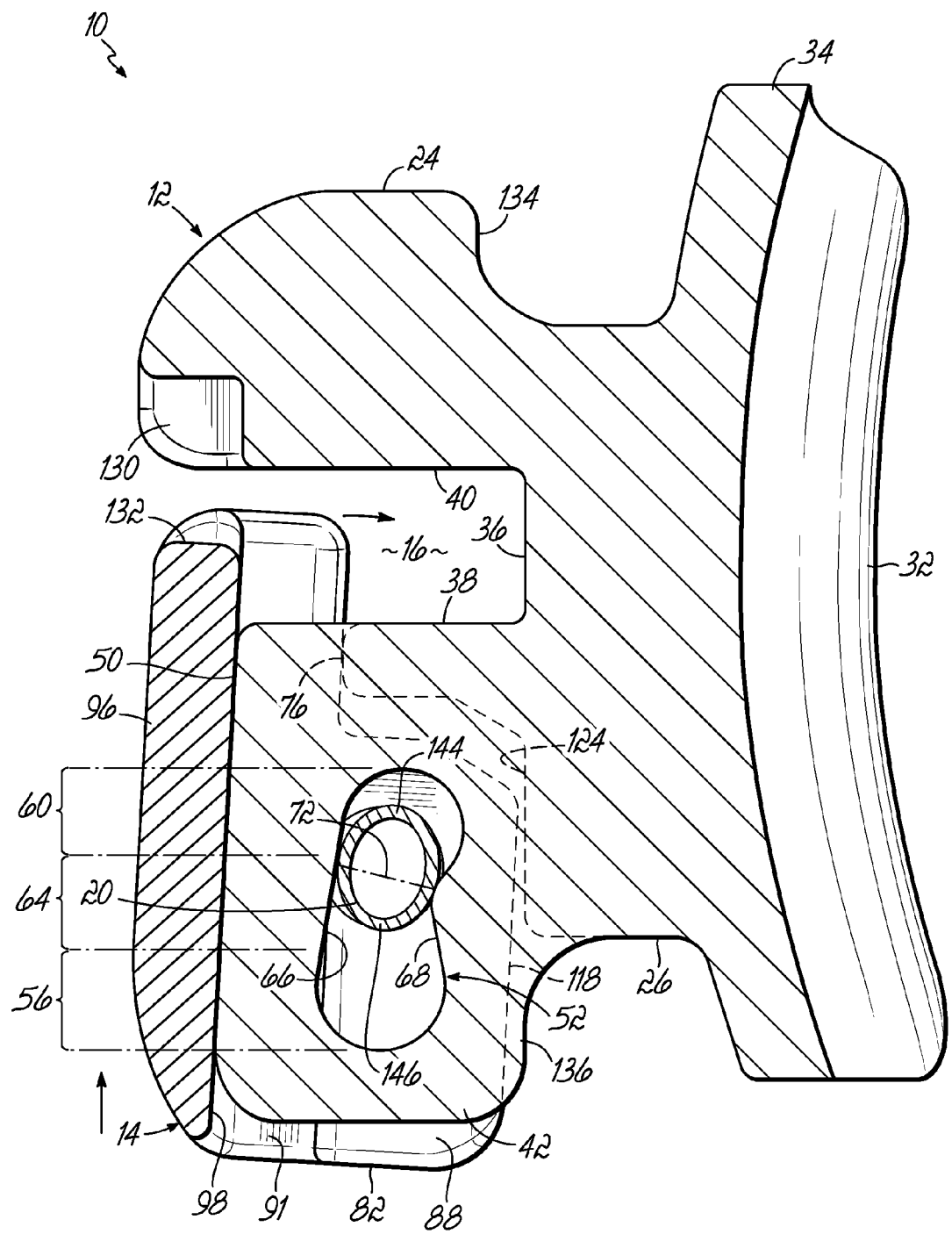
FIG. 9C is a cross-sectional view of the orthodontic bracket taken along section line 9A-9A of FIG. 2, depicting the slide member in a position different from the position shown in FIG. 9B between the closed position of FIG. 1 and the opened position shown in FIG. 2.

With reference to FIG. 9C, the ligating slide 14 is moved closer to the closed position under a force greater than the force required to deform the resilient member 20 as shown in FIG. 9B. At some force greater than the threshold force required to initially move the slide 14 towards the closed position, the force applied to the slide 14 is sufficient to conform the resilient member 20 to the dimension of the pinch point 72. At this magnitude of force, the resilient member 20 is elastically deformed in the region of contact with the aperture 52 so that the resilient member 20 may at least partially squeeze through the pinch point 72. As shown, the resilient member 20 may elastically deform to an egg-shaped cross section. At the pinch point 72, a leading portion 144 of the resilient member 20 may reside within the second lobe portion 60 while a remaining portion 146 of the resilient member 20 extends into the central portion 64. The resilient member 20 may reside partially in each of the second lobe 60 and the central portion 64. By way of example and not limitation, the force required to move slide 14 to a position where the resilient member 20 partially enters the second lobe portion 60 may exceed about 0.1 kgf (kilogram force), and by way of additional example, this force may be from about 0.2 kgf to about 0.8 kgf or from about 0.5 kgf to about 0.7 kgf, preferably about 0.6 kgf.

With continued reference to FIGS. 9A-9C, the magnitude of the force required to overcome the threshold force and/or the threshold sliding force as the ligating slide 14 moves away from the opened position depends on the configuration of the aperture 52. This force may therefore be selectively varied by changing the configuration of the aperture 52. In this regard, the angle of intersection between the second segment 68 and the first segment 66 may be increased to provide a desired opening force and/or sliding force and the rate at which that force may be increased. Furthermore, the position of the pinch point 72 may be selected to provide a shorter or longer central portion by which the rate of force increase may be changed. The shape of the first and/or second segments 66, 68 may be generally planar to provide a linearly increasing sliding force when the resilient member 20 is in the central portion 64. Alternatively, one or both of the segments 66, 68 may be contoured or curved (not shown) to provide a variable sliding force. The above-described methods for varying the opening and/or sliding force are exemplary.

Figure 9D:
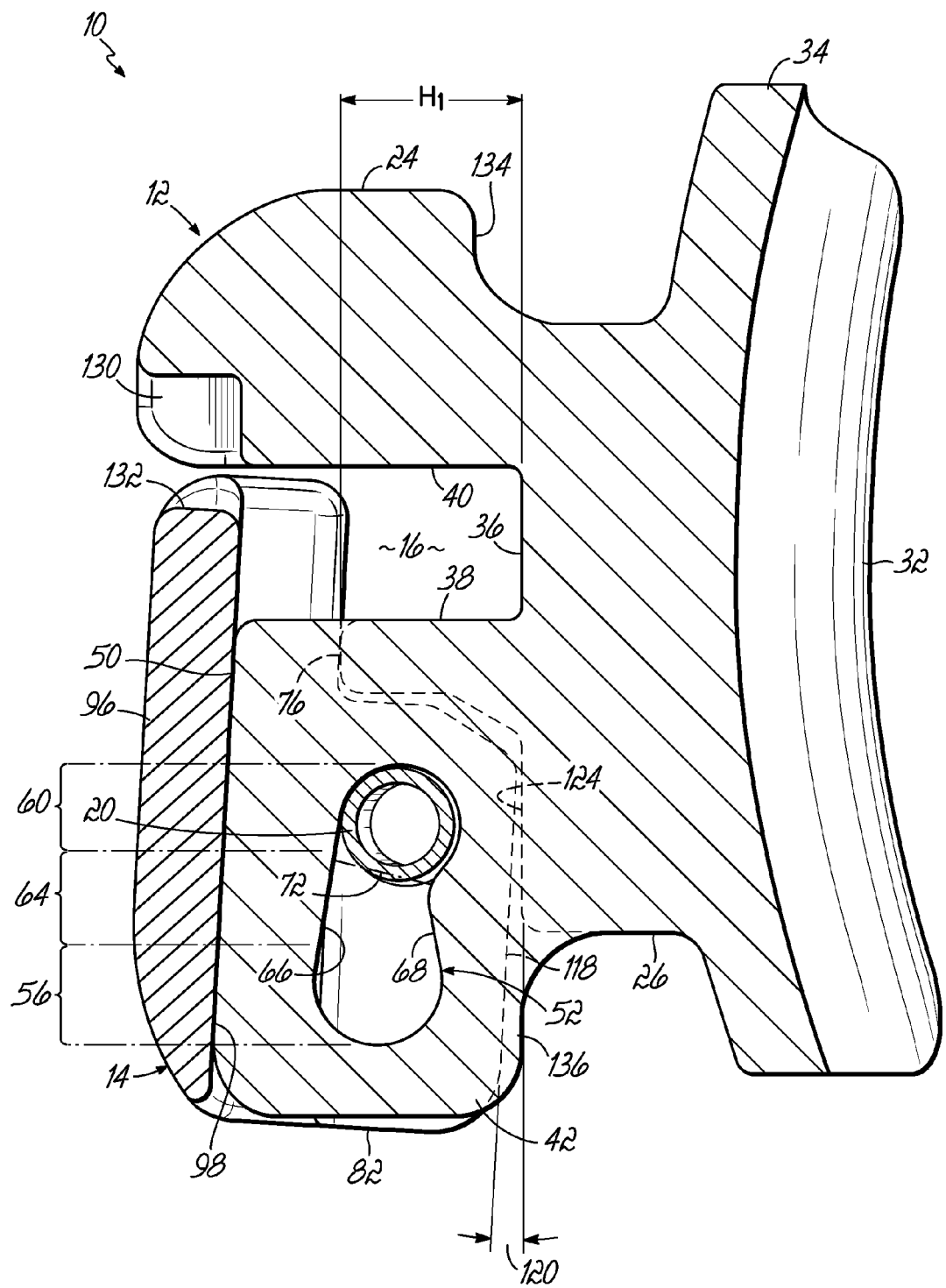
FIG. 9D is a cross-sectional view of the orthodontic bracket taken along section line 9A-9A of FIG. 2, depicting the slide member in the closed position.

Referring now to FIG. 9D, once the opening and/or sliding force meets or exceeds the force required to move the resilient member 20 to a position that is at least partially through the pinch point 72 (as shown in FIG. 9C), the resilient member 20 may spontaneously slide or move the remainder of the distance into the second lobe portion 60. That is, the leading portion 144 and the remaining portion 146 may spontaneously move completely into the second lobe portion 60 in the absence of additional external force. More specifically, once a threshold portion of the resilient member 20 enters the second lobe portion 60, the sliding movement of the resilient member 20 into the second lobe portion 60 may proceed spontaneously. This movement may be accompanied by an audible and/or a tactile "click" or "snap" when the resilient member 20 expands into the second lobe portion 60. By this feature, the clinician may then be assured that the ligating slide 14 has reached its closed position and will remain in the closed position under normal forces observed during the orthodontic treatment.

It is believed that the elastic nature of the resilient member 20 causes a natural inclination for the resilient member 20 to return to an undeformed or at least a less deformed configuration than the deformed configuration of the resilient member 20 in the vicinity of the pinch point 72. Thus, when a threshold portion of the resilient member 20 enters the second lobe portion 60 of the aperture 52, the member 20 may spontaneously release internal elastic energy (by virtue of its deformed condition). Such a release causes the resilient member 20 in the vicinity of the pinch point 72 to move into and fill the second lobe portion 60 without application of additional external force. In other words, only a fractional portion of the resilient member 20 may enter the second lobe portion 60 when an external force is applied to the slide 14 to move the slide 14 to the pinch point 72. The resilient member 20 may move the remainder of the distance into the second lobe portion 60 to revert to a configuration having less or no elastic deformation.

In one embodiment, should an insufficient force be applied to the resilient member 20 so that it fails to enter the second lobe portion 60, the slide 14 may move, in the absence of an external force, toward the opened position because the resilient member 20 may gradually expand into the larger regions of the central region 64 proximate the first lobe portion 56. Ultimately, the resilient member 20 may enter the first lobe portion 56.

Figure 10:
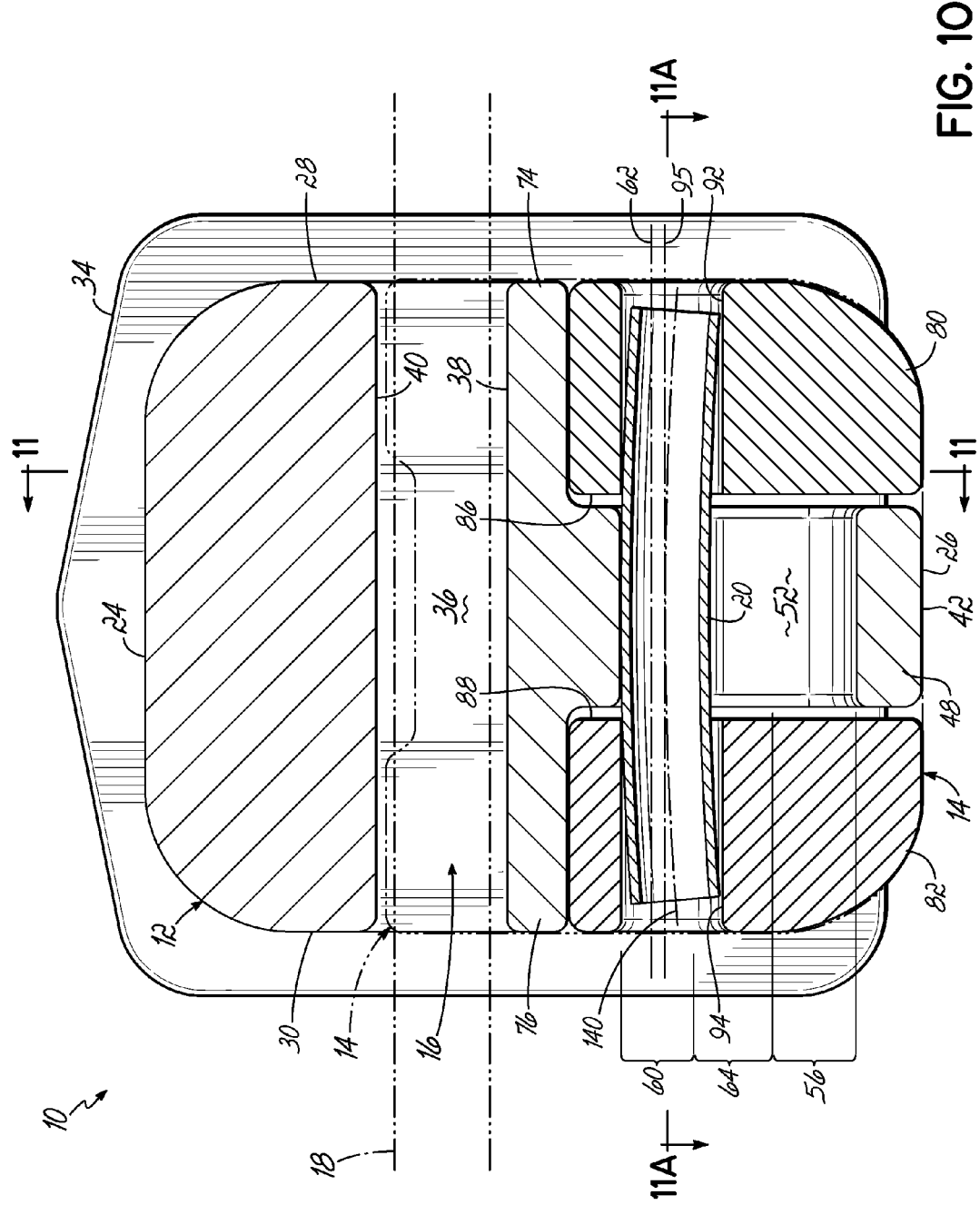
FIG. 10 is a cross-sectional view of the orthodontic bracket shown in FIG. 8 taken along section line 10-10.

In one embodiment and with reference to FIGS. 9D and 10, the ligating slide 14 is shown in the closed position. However, the bores 92, 94 are not fully aligned with the second lobe portion 60 of the aperture 52. In particular, while the slide 14 is in the closed position, the bores 92, 94 are offset from the second lobe portion 60. The offset may be in the occlusal-gingival direction. Specifically, the bores 92, 94 are further away from the archwire slot 16 than the second lobe portion 60.

In one embodiment, the axis 95 of the bores 92, 94 is at a greater distance from the archwire slot 16 than the axis 62 of the second lobe portion 60 when the ligating slide 14 is in a closed position. Nevertheless, even with an offset relationship, the resilient member 20 may spontaneously expand into the second lobe portion 60 to release some of the elastic deformation produced by the pinch point 72. That is, less than 100% of the elastic deformation may be released. As a result, when the central portion of the resilient member 20 is in the second lobe portion 60, the resilient member 20 may be elastically deformed along its axis 140, due to the offset between axis 62 and 95, as is shown in FIG. 10. It is believed that lack of alignment between the bores 92, 94 and the second lobe portion 60 causes the resilient member 20 to be bowed or curved (shown best in FIG. 10). Because the resilient member 20 may be slightly bowed due to the offset in the axes 62 and 95, either end of the resilient member 20 in contact with the ligating slide 14 is biased in a direction toward the archwire slot 16. So, while the resilient member 20 may spontaneously expand into the second lobe portion 60, to release the stored elastic deformation energy from forced movement from the opened position to the pinch point 72, the resilient member 20 may retain some elastic deformation in the closed position. However, the amount of elastic deformation may be less than the amount observed at the pinch point 72.

As set out above, once the slide 14 is in a closed position (FIG. 9D), the elastic deformation in the resilient member 20 produces a bias in the slide 14 in the direction of motion of the slide 14, for example, in the direction of the archwire slot 16. In one embodiment, the bias in the resilient member 20 is in the direction of the slide track 70. In this regard, the bias may be in a direction that intersects a plane that includes the base surface 36 of the archwire slot 16. The bias in the resilient member 20 must be overcome before the slide 14 is movable toward the opened position. Because the applied force must first overcome the bias that is the result of elastic deformation of the resilient member 20, the resilient member 20 provides more consistent contact between the slide 14 and the bracket body 12. For example, the bias may provide more consistent contact between the lingually-facing surfaces 110, 112 and the shoulders 74, 76. Advantageously, the depth of the archwire slot 16 in the generally labial-lingual direction is determined by the position of the shoulders 74, 76 relative to the base surface 36 of the archwire slot 16. Due to the biasing of the ligating slide 14 against shoulders 74, 76 other tolerance variations may no longer have a bearing on the close fit between the archwire slot lumen and the archwire 18.

Figure 11:
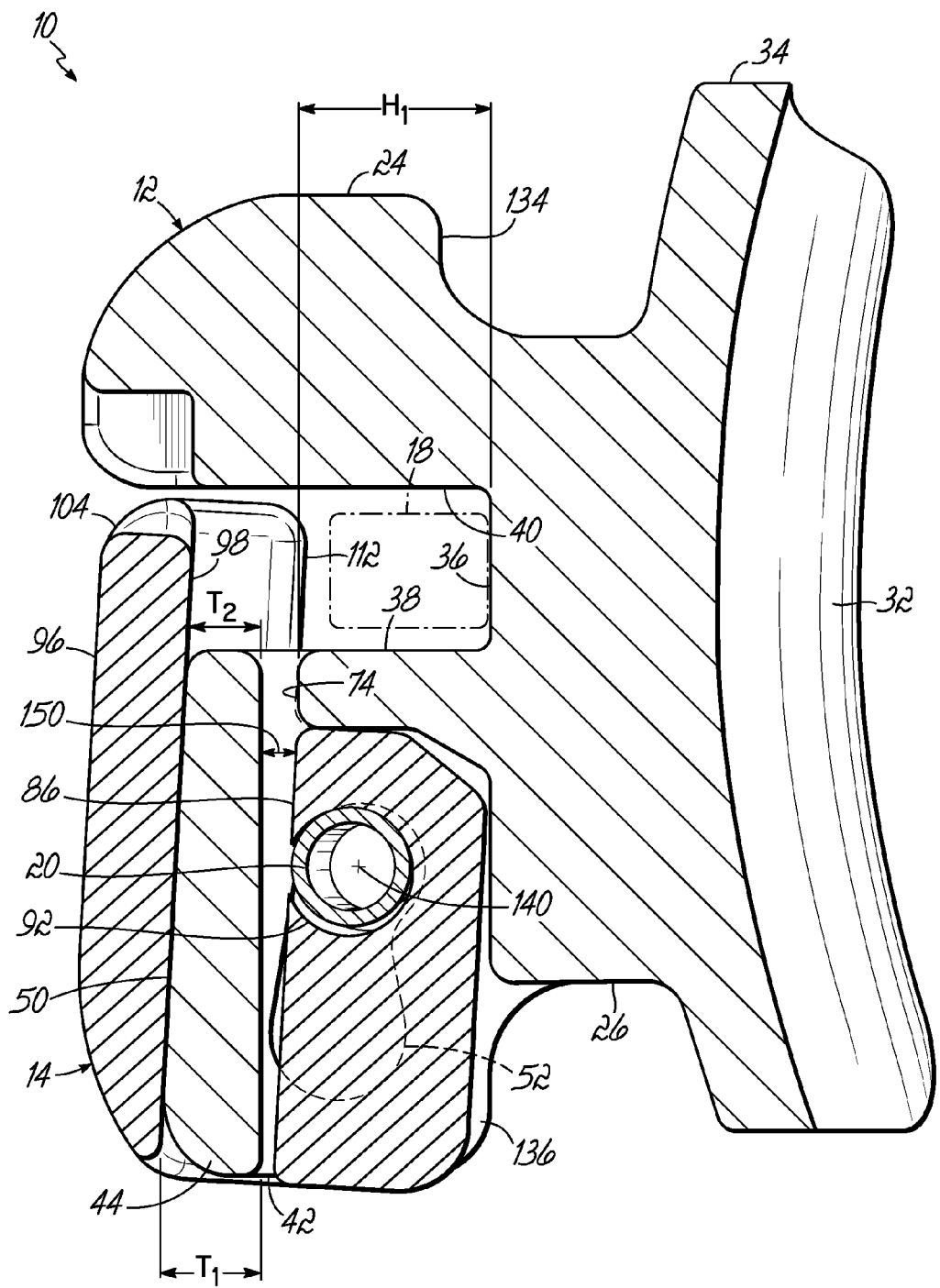
FIG. 11 is a cross-sectional view of the orthodontic bracket shown in FIG. 8 taken along section line 11-11 in FIG. 10.

In this configuration, and with reference to FIG. 11, when the ligating slide 14 is in the closed position and the archwire 18 is dimensioned to be less than H1 the lingually-facing surfaces 110, 112 may not contact the archwire 18, as shown. Rather, the surfaces 110, 112 contact the shoulders 74, 76. It will be appreciated that this configuration may be observed during treatment where it is desired to passively ligate the archwire 18. By way of example only, and not limitation, H1 may be from about 0.018 inch to about 0.022 inch.

As is shown in FIG. 11, there is a clearance or gap 150 between the tapered wing 44 and the shoulder 86 adjacent the shoulder 74. The gap 150 may be tapered or wedge-shaped and correspond to the difference in shape between the tapered wing 44 and the uniform recess 90 (FIG. 7). Further in this regard, the tapering of the gap 150 may be oriented in the gingival-occlusal direction opposite the taper of the tapered wing 44. The gap 150 may be greatest between the occlusal-most edge of the shoulder 86 and the wing 44 and narrowest at the gingival side 26. A similar gap (not shown) may occur between the tapered wing 46 and the shoulder 88.

While there may be gaps between the shoulders 86, 88 and the corresponding tapered wings 44, 46, the ligating slide 14 may slidably engage the slide support portion 42. In particular, the cover portion 96 may slidably engage the support surface 50. As described above, the resilient member 20 may bias the ligating slide 14 in the direction of the archwire slot 16 and particularly in the direction toward the base surface 36. The bias produced by the resilient member 20 may forcibly hold the cover portion 96 against the support surface 50 over at least a portion of the sliding movement from the opened position toward the closed position.

As set out above, contact between the support surface 50 and the cover portion 96 may depend on any angular differences between the support surface 50 and the slide track 70. Specifically, in one embodiment, as the ligating slide 14 contacts one or both of the shoulders 74, 76, a portion of the sliding surface 98 may be slightly displaced from the support surface 50. It will be appreciated that this may ensure contact between one or both of the shoulders 74, 76 and the lingually-facing surfaces 110, 112.

As described above, the ligating slide 14 is slidable relative to the archwire slot 16 and is also pivotable relative to the archwire slot 16. The ligating slide 14 may therefore have multiple closed positions in which the archwire 18 is retained. For example, the ligating slide 14 may have one closed position in which one or both of the lingually-facing surfaces 110, 112 contact a corresponding shoulder 74, 76. As described above, the resilient member 20 may bias the ligating slide 14 against one or both of the shoulders 74, 76.

The ligating slide 14 may pivot to at least one other closed position. In one embodiment of the invention and with reference to FIGS. 11-12A, the ligating slide 14 is movable in an outward or labial direction generally away from the base surface 36 of the archwire slot 16. This outward direction may be generally transverse to the base surface 36 and to the slide track 70 and/or the support surface 50. In one embodiment, this movement is generally perpendicular to the base surface 36 and/or to the slide track 70. The pivotal motion is shown by arrow 152 in FIG. 12. Further, the pivotal motion is against the bias of the resilient member 20. That is, forces on the ligating slide 14 to cause the ligating slide 14 to pivot are resisted by the resilient member 20.

Figure 12:
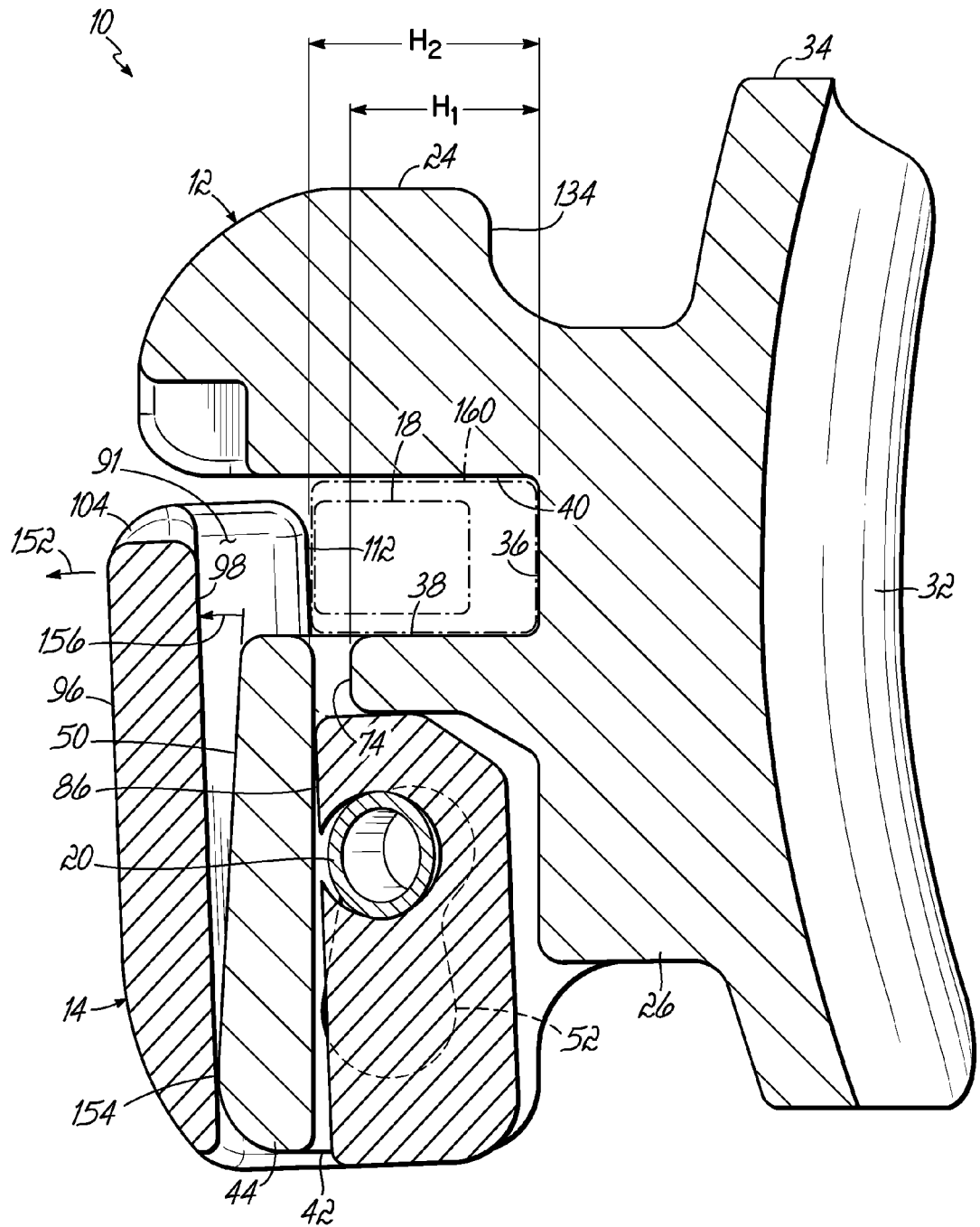
FIG. 12 is a cross-sectional view of the orthodontic bracket shown in FIG. 8 taken along section line 11-11 in FIG. 10 with the slide member shown in another closed position.

There may be at least two reasons that the ligating slide 14 may pivot or move labially relative to the archwire slot 16. According to one, the pivoting motion may be the result of the archwire 18 within the archwire slot 16 pulling labially against the ligating slide 14. This is depicted in FIG. 12. During treatment, if the force tending to pull the archwire 18 from the archwire slot 16 is greater than the bias imposed on the ligating slide 14 by the resilient member 20, the ligating slide 14 may pivot relative to the archwire slot 16.

More specifically, when the force produced by the archwire 18 on the ligating slide 14 reaches a threshold value, the ligating slide 14 may pivot about a contact point between the ligating slide 14 and the bracket body 12 against the bias produced by the resilient member 20. The mesial and distal ligating portions 102, 104 may rotate about the contact point such that the lingually-facing surfaces 110, 112 lift off of or separate from the shoulders 74, 76. By way of example, the ligating slide 14 may pivot about point 154. As shown, the pivot point 154 may be located between the tapered wing 44 and the cover portion 96 at or near the gingival side 26 of the bracket 10. Although not shown, a similar pivot point may occur between the tapered wing 46 and the ligating slide 14. While pivot points are described, it will be appreciated that these contact locations may be the result of two surfaces contacting one another. Thus, a pivot point is not to be strictly construed as a point contact. Rather, contact is between two surfaces and this contact forms a fulcrum through which a load is passed from the ligating slide 14 to the bracket body 12 as the ligating slide 14 pivots away from the base surface 36.

During the pivoting motion about the contact point 154, the shoulder 86 rotates labially to fill the gap 150 (FIG. 11). This movement produces a clearance or gap 156 between the cover portion 96 along the sliding surface 98 and the tapered wing 44. Thus, according to one embodiment, the pivoting motion of the ligating slide 14 about the contact point 154 may reduce the gap 150 while proportionally increasing the gap 156.

The gap 156 reaches a maximum value when the shoulder 86 contacts the tapered wing 44, as shown in FIG. 12. Contact at this location may bring the labial-most surface of shoulder 86 into contact with a lingually facing surface of the tapered wing 44. Once contact occurs between the shoulder 86 and the bracket body 12 (e.g., on the tapered wing 44 at or near the shoulder 76), the pivoting motion stops. Thus, at some predetermined amount of angular movement about the pivot point 154, the ligating slide 14 no longer rotates. By way of example, the angular movement may be greater than about 5° to about 20° and, by way of further example, may be about 10° degrees to about 20°. It will be appreciated that this angular movement exceeds any labial movement that may be associated with normal tolerance stackup between the ligating slide 14 and the bracket body 12. This type of movement may be on the order of about 5°.

Once contact is made, as shown in FIG. 12, pivotal movement stops and any additional load on the ligating slide 14 is transferred from the ligating slide 14 to the bracket body 12 at contact point 154 and at other contacts points between the shoulder 86 and the tapered wing 44. The reverse rotational movement of the ligating slide 14 may also occur.

In this regard, it will be appreciated that as the tooth moves closer to its aesthetically pleasing position, the archwire 18 may move back toward the base surface 36 and may separate from the lingually-facing surfaces 110, 112. As the archwire 18 moves in this direction, the gap 156 decreases while the gap 150 proportionally increases until the lingually-facing surfaces 110, 112 contact corresponding shoulder 74, 76, as shown in FIG. 11. The sliding surface 98 may also contact the support surface 50, particularly at or near the gingival-most portion of the tapered wing 44.

The ligating slide 14 may pivot outwardly in another condition. In one embodiment, an archwire having a greater dimension than H1 may be usable with the bracket 10 and thereby require the ligating slide 14 to pivot outwardly similar to that described in the preceding paragraph. The relatively large archwire may be greater in dimension than the predetermined archwire size represented by dimension H1. As described above, H1 is the labial-lingual dimension from the base surface 36 to the shoulders 74, 76. In view of the pivoting feature of the ligating slide 14, and with reference to FIG. 12, when contact occurs between the ligating slide 14 and the cover portion 96 at contact point 154 and between the shoulder 86 and the tapered wing 44, as described above, the ligating slide 14 may reach its maximum pivotal displacement from the archwire slot 16. In this orientation, the lingually-facing surfaces 110, 112 may be displaced from the base surface 36 by a dimension H2 (labeled in FIG. 12), which may represent the maximum buccal-lingual dimension of an archwire insertable into the archwire slot 16. Thus, the bracket 10 may ligate archwires having buccal-lingual dimensions smaller than H2.

By way of example, an archwire 160 having a dimension of H2 which is greater than H1, will cause the ligating slide 14 to pivot. By way of example and not limitation, where H1 measures about 0.020 inch, the relatively large archwire 160 is larger than 0.020 inch. For example, the relatively large archwire 160 may have a buccal-lingual dimension of about 0.022 inch or a buccal-lingual dimension of about 0.025 inch. When an archwire having a buccal-lingual dimension greater than H1 is used, the ligating slide 14 may slide on the archwire during sliding movement of the ligating slide 14 between the opened and closed position. In this regard, the leading surfaces 106, 108 of the ligating slide 14 may be rounded to allow the ligating slide 14 to climb over the archwire 16 during translational movement toward the closed position.

A clinician may therefore utilize a small archwire, such as archwire 18 shown in FIG. 11 during the initial stages of treatment in which it is desirable to passively ligate the archwire 18. The relatively small archwire 18 may allow for gross tooth movement desired during the initial stages of orthodontic treatment. During the latter stages of orthodontic treatment, the clinician may remove the archwire 18 and insert a relatively large archwire, such as, the archwire 160, into the archwire slot 16. As shown, the archwire 160 may substantially completely fill the archwire slot 16 so as to be continuously actively ligated by the ligating slide 14. The archwire 160 may provide improved rotational or other fine positioning control of the teeth typically desired during the later stages of orthodontic treatment.

Figure 11A:
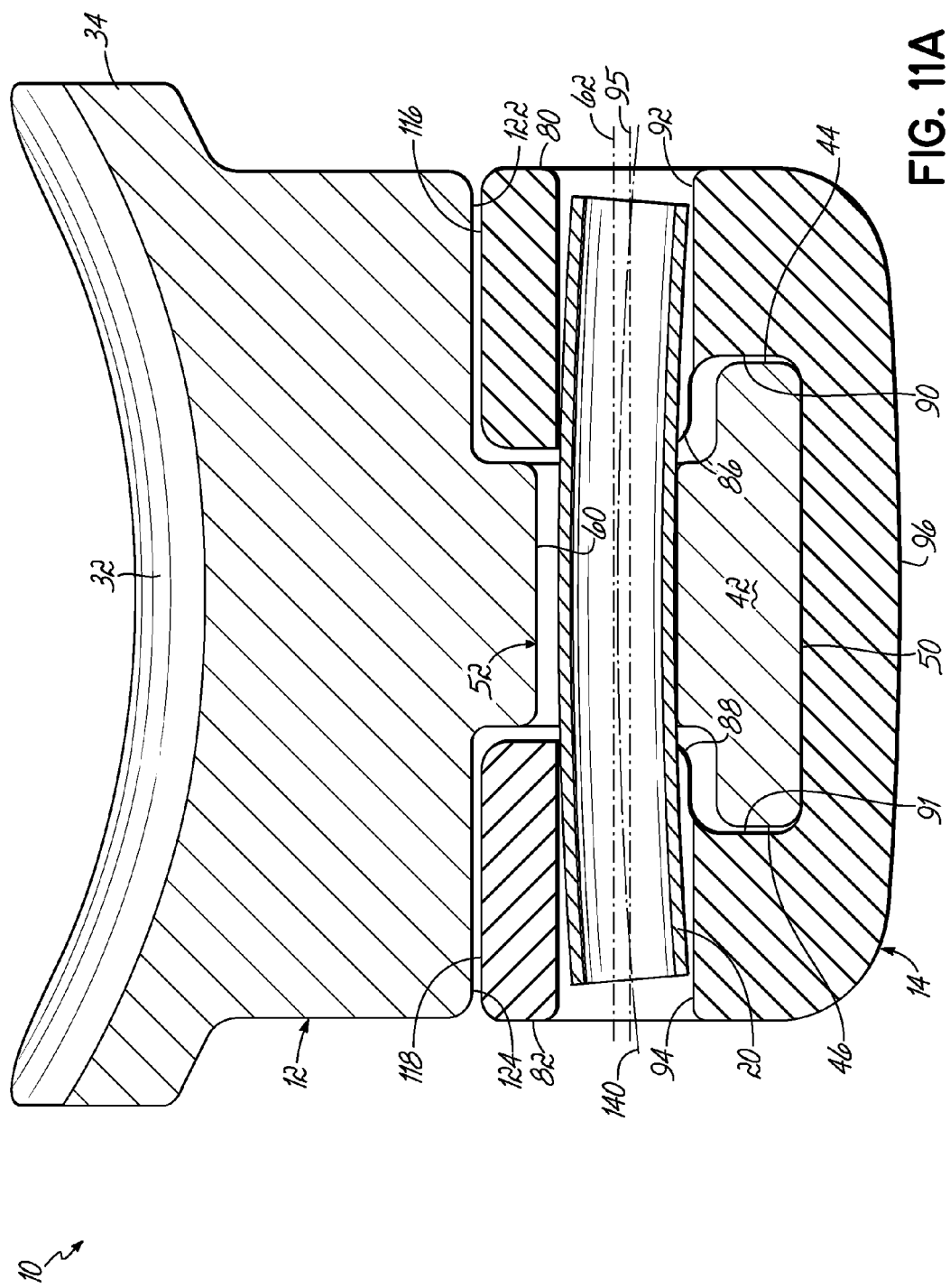
FIG. 11A is a cross-sectional view of the orthodontic bracket shown in FIG. 8 taken along section line 11A-11A in FIG. 10.
Figure 12A:
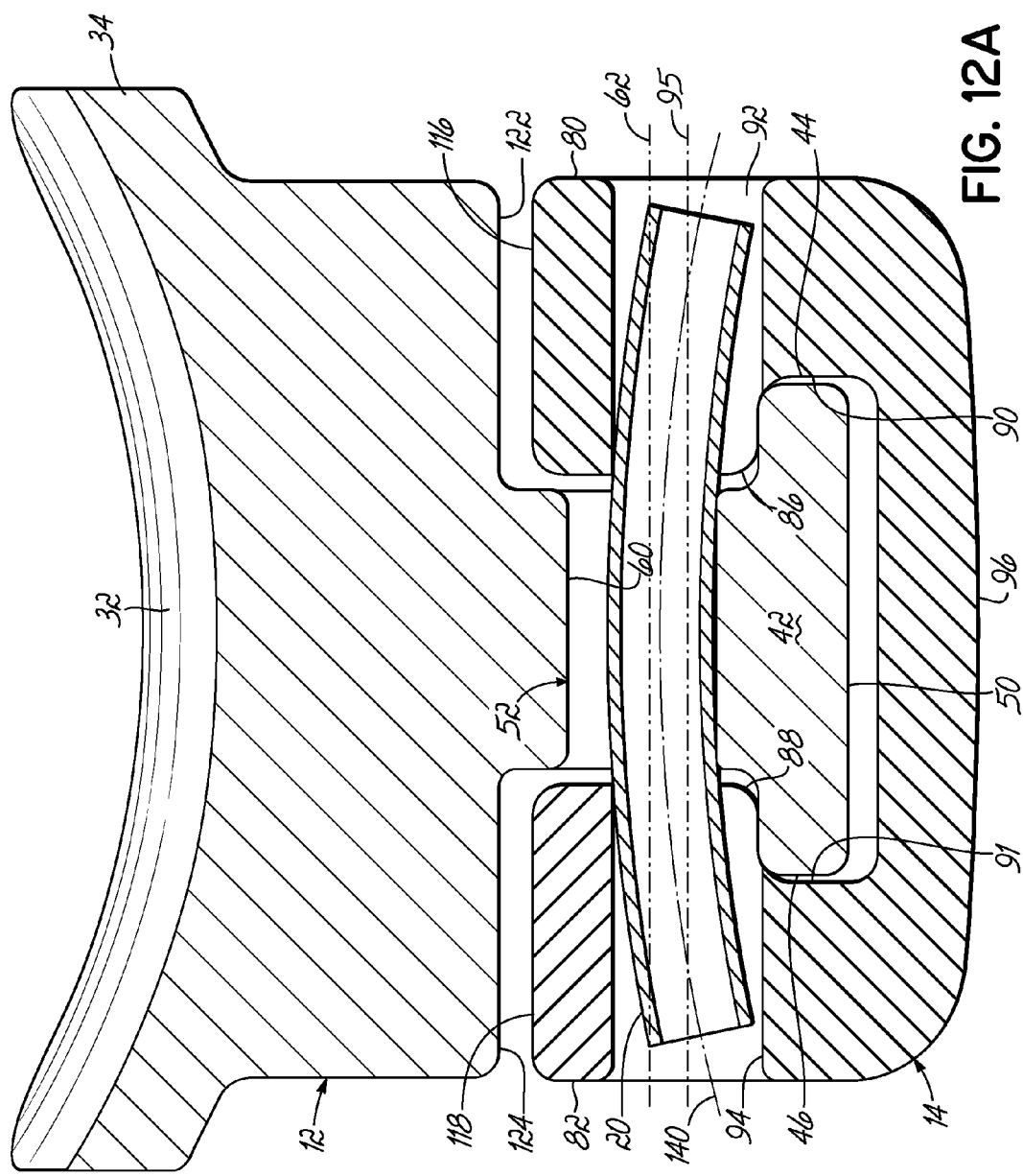
FIG. 12A is a cross-sectional view of the orthodontic bracket taken along section line 11A-11A in FIG. 10, depicting the slide member pivoted outward as shown in FIG. 12.

It will be appreciated that in the configuration shown in FIG. 12, the ligating slide 14 actively ligates the archwire 160 because the archwire 160 is larger than H1 causing the resilient member 20 to elastically deform to a greater degree than the deformation obtained when the ligating slide 14 is in contact with the shoulders 74, 76. Elastic deformation of the resilient member 20 may be in a labial-lingual direction, as is depicted in FIGS. 11A and 12A. By way of example only, without being bound to any theory, it is believed that elastic deformation is lengthwise along the longitudinal axis 140 with the opposing ends of the resilient member 20 in the mesial and distal through-bores 92, 94 being bent labially relative to the portion of the resilient member 20 in the second lobe portion 60. With regard to FIG. 11A, when the ligating slide 14 is in the closed position with the lingually-facing surfaces 110, 112 in contact with the corresponding shoulders 74, 76, the resilient member 20 may be bent slightly along its longitudinal axis 140, as shown, with opposing ends of the resilient member 20 being positioned labially of the portion of the resilient member 20 positioned in the aperture 52.

With reference to FIGS. 11A and 12A, the resilient member 20 may be elastically deformed to a greater degree in FIG. 12A compared to FIG. 11A as the ligating slide 14 pivots. Specifically, the opposing ends of the resilient member 20 may further deflect labially such that the axis 95 may be further displaced labially of the axis 62 of the second lobe portion 60 by an amount related to the distance between the shoulders 74, 76 and the contact location between the shoulders 86, 88 and the corresponding tapered wings 44, 46. It will be appreciated that as the magnitude of the elastic deformation of the resilient member 20 increases, because larger and larger archwires (up to a predetermined maximum) may be inserted into the archwire slot 16, the biasing force on each correspondingly larger archwire increases. This is illustrated by way of comparison between FIGS. 11A and 12A in which the resilient member 20 is deformed to a greater degree in FIG. 12A than in FIG. 11A by virtue of the large archwire 160 in the archwire slot 16 as compared to the archwire 18 in the archwire slot 16 in FIG. 11A.

In addition to the lengthwise elastic deformation of the resilient member 20 during the pivoting motion, the resilient member 20 may also deform elastically through its cross section. This is shown best by way of comparison of FIGS. 11 and 12. When the ligating slide 14 rests against the shoulders 74, 76, the resilient member 20 may be only slightly deformed across its cross section. As the ligating slide 14 is lifted from the position shown in FIG. 11 towards the fully pivoted position shown in FIG. 12, the resilient member 20 may be elastically compressed across its cross section with the diameter dimension in the labial-lingual direction being compressed and the diameter dimension in the occlusal-gingival direction being correspondingly expanded. As shown in FIG. 12, the resilient member 20 may be deformed to an oval-like or egg-shaped cross section configuration (shown exaggerated in FIG. 12) when the ligating slide 14 reaches its maximum pivot location. This cross sectional deformation may be localized to an area in the immediate proximity of the bores 92, 94 and the aperture 52. When the ligating slide 14 is fully pivoted, it will be appreciated that the resilient member 20 produces a maximum bias on the archwire in the archwire slot 16.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. An orthodontic bracket for coupling an archwire with a tooth, comprising:
   a bracket body that includes an aperture and an archwire slot;
   a rigid ligating slide that is slidable relative to the archwire slot between an opened position and a first closed position and is pivotable relative to the archwire slot to a second closed position, the second closed position being different from the first closed position; and
   a resilient member that is coupled to the ligating slide and is slidable in the aperture,
   wherein the ligating slide pivots as a whole between the first and second closed positions.

2. The orthodontic bracket of claim 1 wherein when the ligating slide is pivoted from the first closed position to the second closed position, an angle is formed between the ligating slide and the bracket body that is greater than about 5° to about 20°.

3. The orthodontic bracket of claim 1 wherein when the ligating slide is pivoted from the first closed position to the second closed position, an angle is formed between the ligating slide and the bracket body that is from about 10° to about 20°.

4. The orthodontic bracket of claim 1 wherein the archwire slot includes opposed slot surfaces extending from a base surface and in the first closed position, the ligating slide defines a first height from the base surface to the ligating slide and in the second closed position, the ligating slide defines a second height from the base surface to the ligating slide that is from about 0.002 inch to about 0.005 inch greater than the first height.

5. The orthodontic bracket of claim 1 wherein the bracket body includes a slide support portion defining a pivot point about which the ligating slide pivots from the first closed position to the second closed position and having at least one wing extending laterally therefrom, the at least one wing being tapered in thickness along the length thereof, the taper of the wing determining a first gap between the slide support portion and the ligating slide in the first closed position and a second gap between the slide support portion and the ligating slide in the second closed position.

6. The orthodontic bracket of claim 5 wherein the ligating slide includes a uniformly dimensioned recess and the at least one wing resides within the uniformly dimensioned recess during sliding movement of the ligating slide.

7. The orthodontic bracket of claim 6 wherein the uniformly dimensioned recess defines a shoulder and at the second closed position the shoulder contacts the at least one wing.

8. The orthodontic bracket of claim 7 wherein the first gap is between the shoulder and the wing.

9. The orthodontic bracket of claim 1 wherein the bracket body includes a support surface and the ligating slide includes a sliding surface that faces the support surface when the ligating slide is in the first closed position, and when the ligating slide is pivoted to the second closed position, the support surface and the sliding surface contact at a pivot point and an angle of greater than about 5° to about 20° is formed between the support surface and the sliding surface at the pivot point.

10. The orthodontic bracket of claim 9 wherein the pivot point is at a peripheral edge of the support surface.

11. The orthodontic bracket of claim 1 wherein the resilient member imposes a biasing force on the ligating slide in each of the first closed position and the second closed position.

12. The orthodontic bracket of claim 1 wherein the ligating slide does not pivot about the resilient member.

13. The orthodontic bracket of claim 1 wherein the ligating slide includes a bore and the resilient member is received in the bore and extends from the bore into the aperture.

14. An orthodontic bracket for coupling an archwire with a tooth, comprising:
   a bracket body that includes an archwire slot;
   a ligating slide that is slidable relative to the archwire slot between an opened position and a first closed position and is pivotable relative to the archwire slot to a second closed position, the second closed position being different from the first closed position; and
   a resilient member having opposed ends, each end being coupled to the ligating slide, and an intermediate portion that slidably couples the ligating slide to the bracket body.

15. The orthodontic bracket of claim 14 wherein the resilient member is a tubular pin.

16. The orthodontic bracket of claim 14 wherein a longitudinal axis of the resilient member extends generally parallel to the archwire slot in the opened position.

17. The orthodontic bracket of claim 16 wherein the resilient member is bent along the longitudinal axis in at least one of the closed positions.

18. The orthodontic bracket of claim 14 wherein the ligating slide includes a mesial portion and a distal portion that each extend from a cover portion and define a slide channel therebetween, each end of the resilient member being coupled to a respective one of the mesial portion and the distal portion with the intermediate portion extending between the mesial portion and the distal portion across the slide channel.

19. An orthodontic bracket for coupling an archwire with a tooth comprising:
   a bracket body that includes an archwire slot;
   a ligating slide that is slidable relative to the archwire slot between an opened position and a first closed position and is pivotable relative to the archwire slot to a second closed position, the second closed position being different from the first closed position; and
   a resilient member that is coupled to the ligating slide and is slidable relative to the bracket body, and when the ligating slide is in the opened position, a longitudinal axis of the resilient member extends generally parallel to the archwire slot.

20. The orthodontic bracket of claim 19 wherein the resilient member is a tubular pin.

21. The orthodontic bracket of claim 19 wherein the resilient member is bent along the longitudinal axis in at least the first closed position.

22. The orthodontic bracket of claim 19 wherein the resilient member has opposed ends, each end being coupled to the ligating slide, and an intermediate portion that slidably couples the ligating slide to the bracket body.

23. The orthodontic bracket of claim 22 wherein the ligating slide includes a mesial portion and a distal portion that each extend from a cover portion and define a slide channel therebetween, each end of the resilient member being coupled to a respective one of the mesial portion and the distal portion with the intermediate portion extending between the mesial portion and the distal portion across the slide channel.

* * * * *